United States Patent
Sartor et al.

(10) Patent No.: US 11,905,267 B2
(45) Date of Patent: Feb. 20, 2024

(54) HIGH TRIPLET YIELD PHENOTHIAZINE DONOR-ACCEPTOR COMPLEXES FOR PHOTOREDOX CATALYSIS

(71) Applicants: The Regents of the University of Colorado, Denver, CO (US); Colorado State University Research Foundation, Fort Collins, CO (US)

(72) Inventors: Steven Sartor, Boulder, CO (US); Niels Damrauer, Boulder, CO (US); Garet Miyake, Fort Collins, CO (US); Cameron Chrisman, Fort Collins, CO (US); Ryan Pearson, Berkeley, CA (US)

(73) Assignees: THE REGENTS OF THE UNIVERSITY OF COLORADO, A BODY CORPORATE, Denver, CO (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 17/789,874

(22) PCT Filed: Jan. 8, 2021

(86) PCT No.: PCT/US2021/012732
§ 371 (c)(1),
(2) Date: Jun. 29, 2022

(87) PCT Pub. No.: WO2021/142287
PCT Pub. Date: Jul. 15, 2021

(65) Prior Publication Data
US 2023/0100472 A1    Mar. 30, 2023

Related U.S. Application Data

(60) Provisional application No. 62/958,611, filed on Jan. 8, 2020.

(51) Int. Cl.
*C07D 279/30* (2006.01)
*C07D 279/24* (2006.01)

(52) U.S. Cl.
CPC ......... *C07D 279/30* (2013.01); *C07D 279/24* (2013.01)

(58) Field of Classification Search
CPC .......................... C07D 279/30; C07D 279/24
See application file for complete search history.

(56) References Cited

U.S. PATENT DOCUMENTS

2018/0151807 A1    5/2018    Tang et al.

FOREIGN PATENT DOCUMENTS

| CN | 104478870 A | 4/2015 |
| WO | 2015014434 A1 | 2/2015 |

OTHER PUBLICATIONS

Mondal et al. 'Cage Encapsulated Gold Nanoparticles as Heterogeneous Photocatalyst for Facile and Selective Reduction of Nitroarenes to Azo Compounds', Journal of the American Chemical Society, Sep. 10, 2018 (Sep. 10, 2018), vol. 140, pp. 12592-12601; p. 12593.
Chen et al. 'Four-Component Approach to N. Substituted Phenothiazines under Transition-Metal-Free Conditions', Organic Letters, Nov. 23, 2015 (Nov. 23, 2015), vol. 17, pp. 5870.5873; p. 5871.
Pubmed Compound Record for CID 146982827, '3,7,10-Triphenylphenothiazine', U.S. National Library of Medicine, Aug. 12, 2020 (Aug. 12, 2020), pp. 1-8 (https://pubchem.ncbi.nlm.nih.gov/compound/146982827); p. 2.
International Search Report in international application No. PCT/US2021/012732 dated May 19, 2021, 4 pages.
Written Opinion of the International Searching Authority in international application No. PCT/US2021/012732 dated May 19, 2021, 4 pages.

*Primary Examiner* — Paul V Ward
(74) *Attorney, Agent, or Firm* — Berg Hill Greenleaf Ruscitti LLP

(57) ABSTRACT

Phenothiazine compounds of Formula (I) are described herein. These compounds are useful as highly reducing organic photoredox catalysts. Suitable substrates for use with the compounds of Formula (I) include acrylates, styrene, acrylamides, acrylonitrile, vinyl chloride, methylacrylonitrile, vinyl acetate, and acrylic acid.

14 Claims, 12 Drawing Sheets

HIGH TRIPLET YIELD PHENOTHIAZINE DONOR-ACCEPTOR COMPLEXES FOR PHOTOREDOX CATALYSIS

CROSS-REFERENCE TO RELATED APPLICATION

This application is a national stage application under 35 U.S.C. 371 of PCT Application No. PCT/US21/12732 having an international filing date of Jan. 8, 2020, which designated the United States, which PCT application claimed the benefit of U.S. Application Ser. No. 62/958,611, filed Jan. 8, 2020, both of which are incorporated by reference in their entirety.

STATEMENT REGARDING FEDERALLY SPONSORED RESEARCH

This invention was made with government support under grant number GM119702 awarded by the National Institutes of Health; and grant number CHE1339674 awarded by the National Science Foundation. The government has certain rights in this invention.

BACKGROUND

Photoredox catalysis is an increasingly attractive method for achieving challenging chemical transformations under mild synthetic conditions. Presently, however, rare-metal photocatalysts—primarily containing ruthenium or iridium—continue to dominate the field. Continued reliance on these rare metals limits the potential supply of photocatalysts, thus motivating the development of photocatalysts of comparable capability made from earth-abundant elements.

The development of organic photocatalysts is aided by the increased reaction scope that the diversity of organic systems provides. However, organic photocatalysts often suffer from inefficient intersystem crossing (ISC), thus limiting access to the long-lived triplet excited state. This is a significant drawback, as the long-lived triplet state (typically ~$10^3$-$10^6$ times longer-lived than the singlet) affords the photocatalyst sufficient time to efficiently engage in excited-state bimolecular electron transfer. Traditional methods of increasing the yield of ISC ($\Phi_{ISC}$) (e.g., carbonyl or heavy atom functionalization) can be undesirable, as these can increase synthetic complexity, lessen reactive potency, reduce triplet lifetimes, and increase the likelihood of undesirable side reactions.

An alternative to these traditional methods is SOCT-ISC (SOCT=spin-orbit charge transfer) involving a singlet charge transfer (CT) state with orthogonal (or nearly-orthogonal) donor and acceptor moieties. Such systems facilitate efficient ISC by slowing radiative decay and, because the recombination process (undoing the CT) requires a significant change in orbital angular momentum, providing the torque necessary for a change in spin angular momentum to the triplet manifold. Importantly, the SOCT-ISC mechanism does not suffer from the drawbacks stated above for traditional methods for increasing $\Phi_{ISC}$.

The phenothiazine-based photocatalysts described herein solve the need for alternative catalytic systems by acting as photocatalysts for a variety of photocatalytic transformations, including, but not limited to, polymerizing useful monomer substrates without the need for expensive and/or toxic heavy metals.

BRIEF SUMMARY OF THE INVENTION

In various embodiments, a compound of Formula I is provided. The compound of Formula I has the structure:

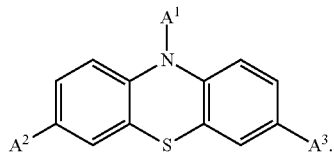

Formula I

In certain embodiments, in the compound of Formula I, each of $A^1$, $A^2$, and $A^3$ is independently an optionally substituted $C_{6-18}$ aryl, wherein the optional substitution is from 1 to 12 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$; wherein R is independently at each occurrence hydrogen or $C_{1-10}$ hydrocarbyl, provided that the compound of Formula I is not:

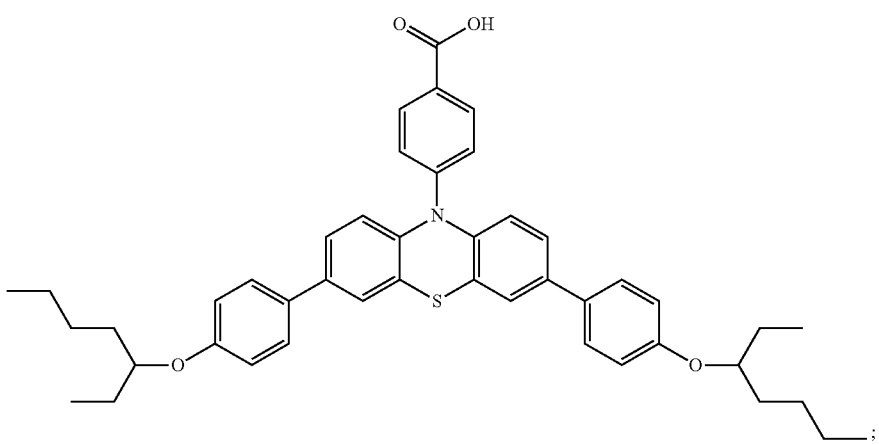

-continued

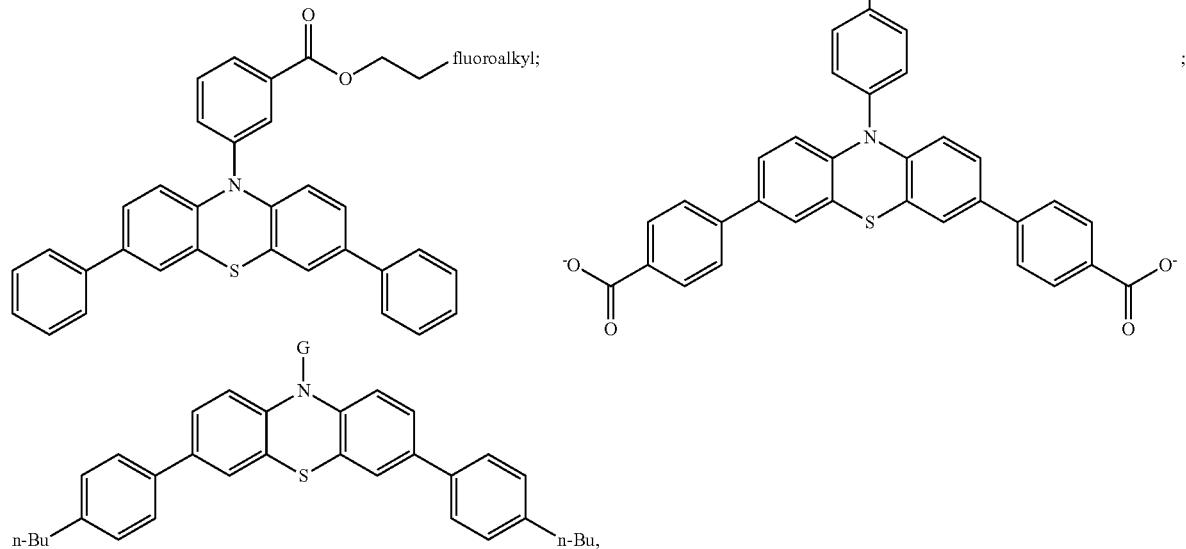

or salts thereof; wherein G is

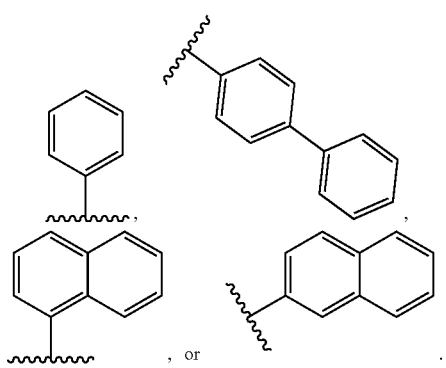

In various embodiments, a method of polymerizing a substrate is provided. The method includes providing a composition comprising at least one monomer and at least one compound of Formula I; and irradiating the composition with electromagnetic radiation, wherein the composition is free from metals. In certain embodiments, the at least one monomer comprises at least one of acrylates, styrene, acrylamides, acrylonitrile, vinyl chloride, methylacrylonitrile, vinyl acetate, acrylic acid, or mixtures thereof.

BRIEF DESCRIPTION OF THE FIGURES

The drawings illustrate generally, by way of example, but not by way of limitation, various embodiments of the present application.

(FIG. 3C) Observed and simulated late-time FSTA spectra of Naph, with the redox-derived data and early-time FSTA spectrum used for simulation. Solid and dashed lines refer to ΔA and absorbance spectra, respectively.

FIGS. 4B and 4C show triplet SOMOS (singly occupied molecular orbital) of Phen (FIG. 4B) and Naph (FIG. 4C) (uM06/6-31g(d,p)/CPCM-DMAc level of theory).

FIGS. 7B and 7C show triplet SOMOS of Fluoro-Naph (FIG. 7B) and Cyano-Naph (FIG. 7C) (uM06/6-31g(d,p)/CPCM-DMAc level of theory).

DETAILED DESCRIPTION OF THE INVENTION

Definitions

Figure 1:
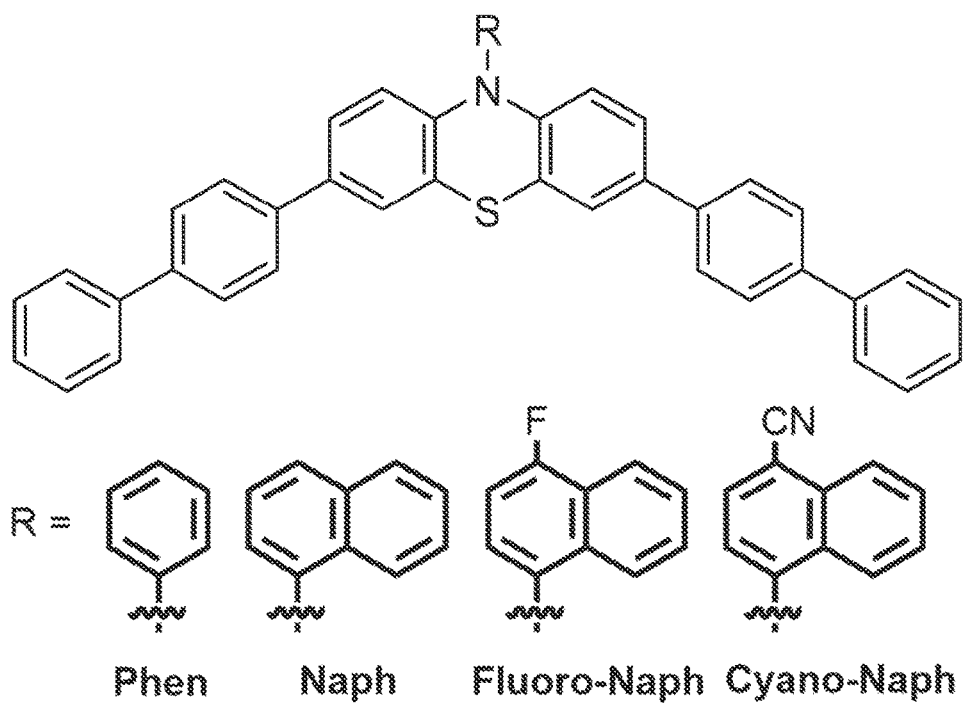
FIG. 1 shows compounds of Formula I according to various embodiments.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7.

Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein.

The phrase also includes polycyclic ring systems containing a heteroatom such as, but not limited to, quinuclidyl. Heterocyclyl groups can be unsubstituted, or can be substituted as $\Phi_{ISC}$ used herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3- pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, epoxypentyl, 2,3-epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2-(4-methyl-3,4-epoxycyclohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a\text{-}C_b)$hydrocarbyl, wherein a and b are integers and mean having any of a to b number of carbon atoms. For example, $(C_1\text{-}C_4)$hydrocarbyl means the hydrocarbyl group can be methyl $(C_1)$, ethyl $(C_2)$, propyl $(C_3)$, or butyl $(C_4)$, and $(C_0\text{-}C_b)$hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 20° C. and 101 kPa.

Compounds

Compounds of the invention or otherwise described herein can be prepared by the general schemes described herein, using the synthetic method known by those skilled in the art. The following examples illustrate non-limiting embodiments of the compound(s) described herein and their preparation.

In one embodiment, a compound of Formula I is provided. The compound of Formula I has the following structure:

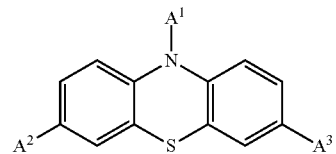

Formula I

In the compound of Formula I, in certain embodiments, each of $A^1$, $A^2$, and $A^3$ is independently an optionally substituted $C_{6-18}$ aryl, wherein the optional substitution is from 1 to 12 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$. Also in the compound of Formula I, in certain embodiments, R is independently at each occurrence hydrogen or $C_{1-10}$ hydrocarbyl. In various embodiments, R is independently methyl, ethyl, n-propyl, i-propyl, n-butyl, s-butyl, t-butyl, pentyl, hexyl, heptyl, nonyl, or decyl, including isomers of the foregoing.

In certain embodiments, each of $A^1$, $A^2$, and $A^3$ is independently selected from the group consisting of

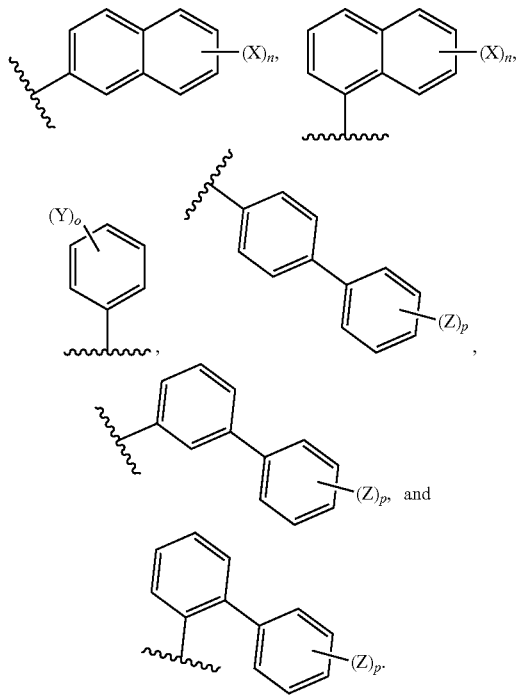

In certain embodiments, each occurrence of X, Y, and/or Z is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$. In some embodiments, each occurrence of X, Y, and/or Z is independently is an electron withdrawing group, which, in some embodiments is defined as a group that contains more electron density than H (hydrogen). Each X, Y, and/or Z can replace an open valence on the ring to which it is attached, and in the case of naphthyl and biphenyl, the attachment can be on any of the rings, not just the ring on which the variable X or Z is depicted on.

Variables 'n', 'o', and 'p' are each integers defined as follows: n is an integer from 0 to 7; o is an integer from 0 to 5; and p is an integer from 0 to 9.

When multiple X, Y, and/or Z variables are present, they may be designated with a numeric subscript. For example, if n is 3, then the X substituents can be designated $X_1$, $X_2$, and $X_3$ and arranged anywhere on the ring to which they are attached where there is an open valence. The same applies for the other variables, depending on the value(s) of n, o, and/or p.

In certain embodiments, n is 1. In certain embodiments, o is 1. In certain embodiments, p is 1.

In various embodiments, each of $A^1$, $A^2$, and $A^3$ is independently selected from the group consisting of

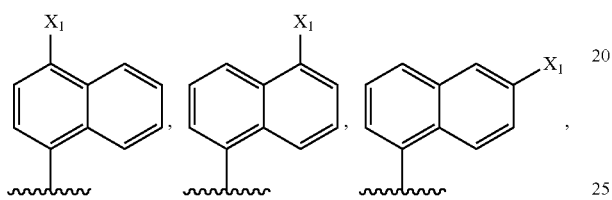

,

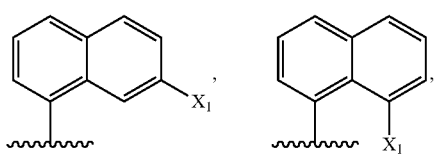

,

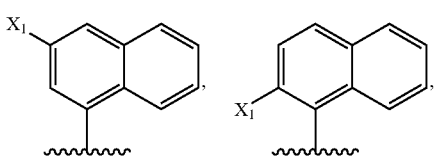

,

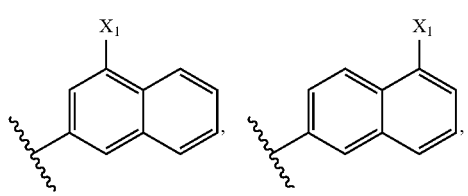

,

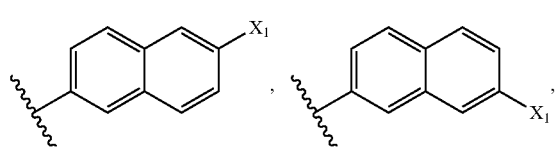

,

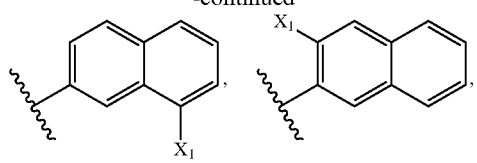

,

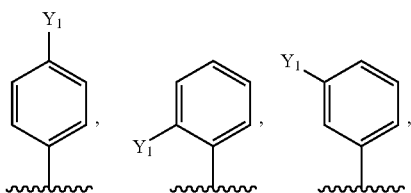

,

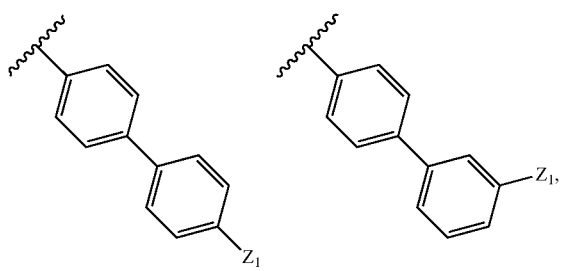

,

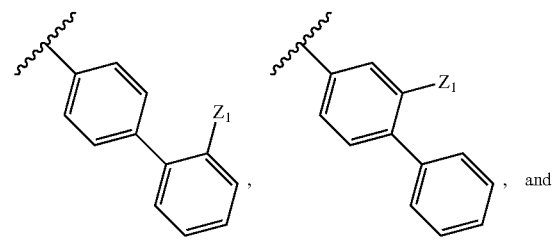

, and

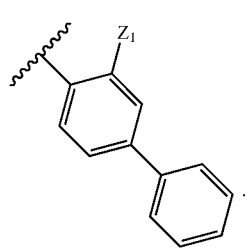

.

In certain embodiments, each of $X_1$, $Y_1$, and $Z_1$ is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$.

In various embodiments, the compound of Formula I is not:
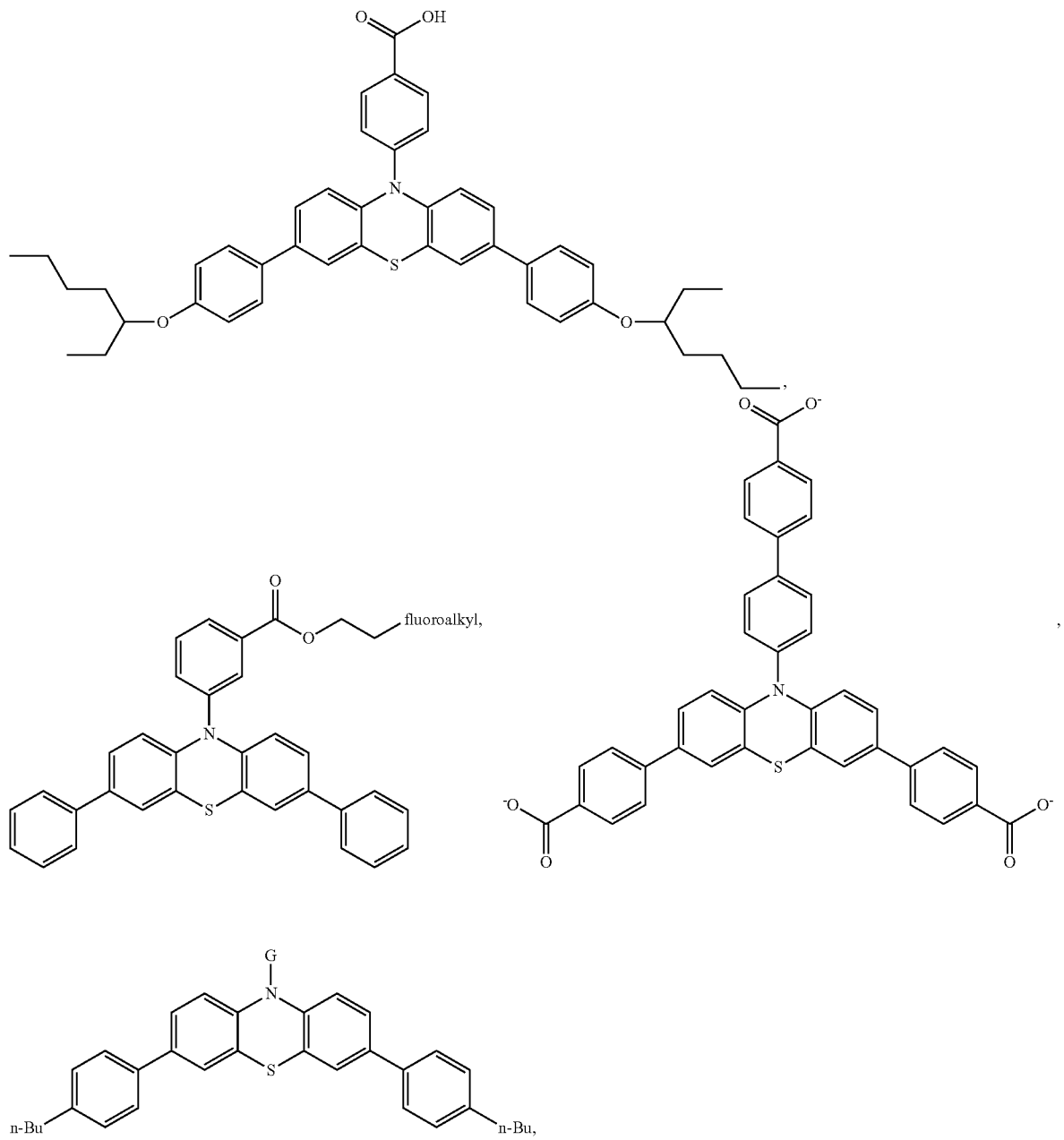
or salts thereof, wherein G is
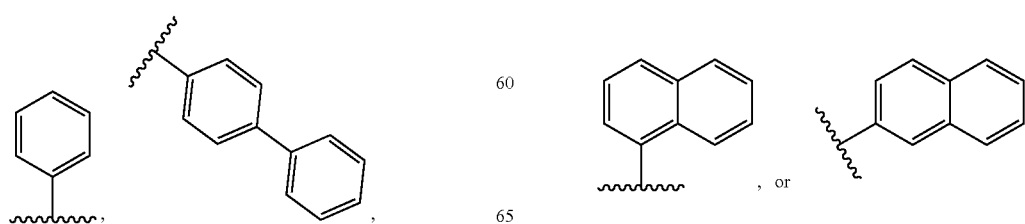

In various embodiments, the compound of Formula I is:

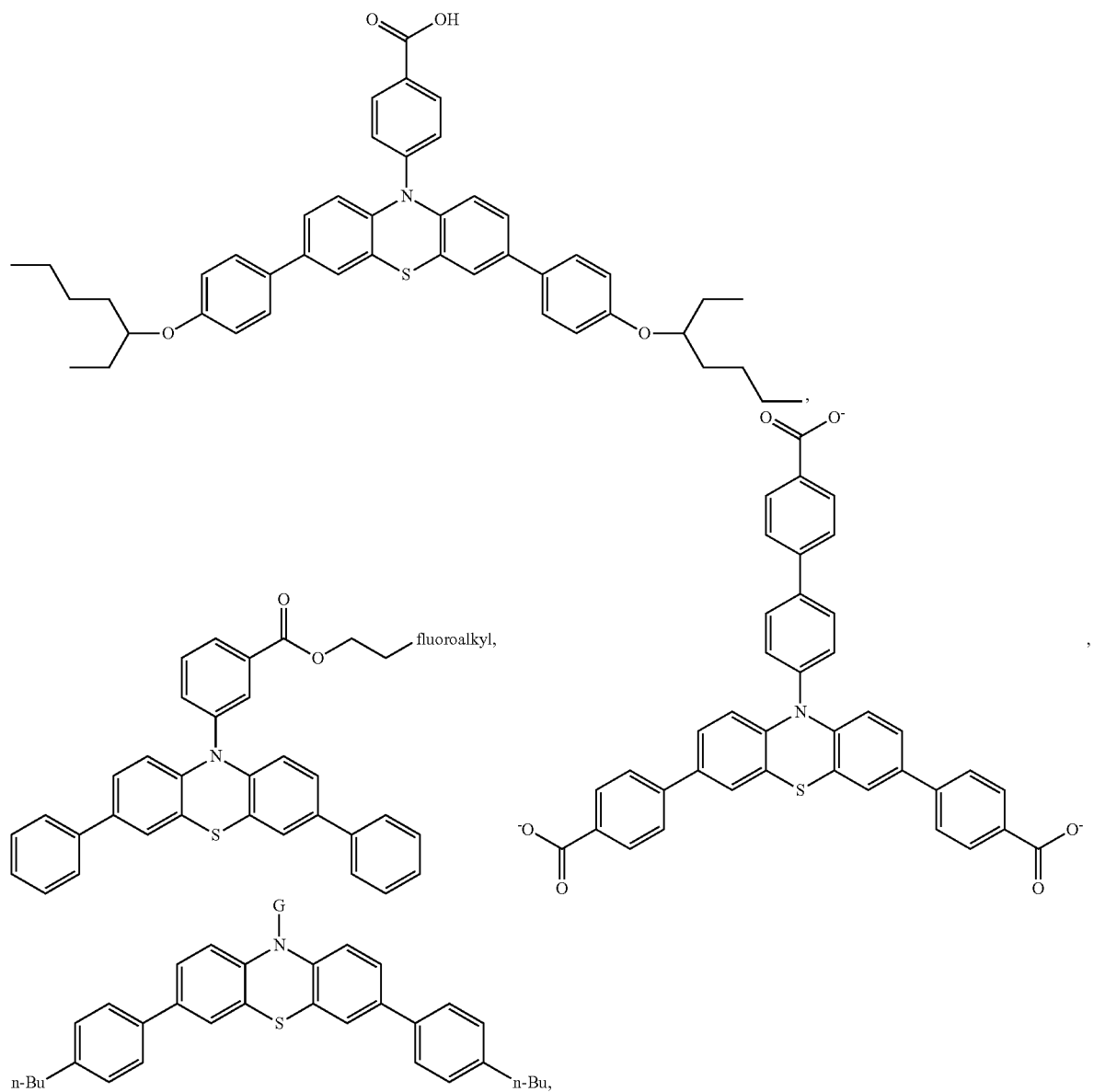

or salts thereof, wherein G is

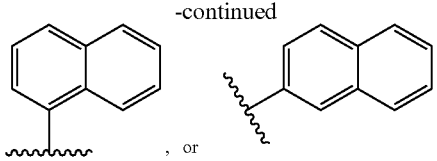

In various embodiments, $A^2$ and $A^3$ are $C_{6-12}$ aryl. In various embodiments, $A^2$ and $A^3$ are biaryl. In some embodiments, $A^2$ and $A^3$ are 4,4'-biphenyl.

In various embodiments, $A^1$ is a $C_{10}$ aryl substituted by 1 to 7 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$.

In various embodiments, $A^1$ is 1-naphthyl or 2-naphthyl. In various embodiments, $A^1$ is

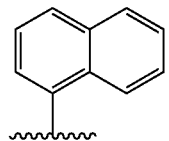

In various embodiments, $A^1$ is 1-naphthyl or 2-naphthyl is mono-substituted by a group selected from the group consisting of F, Cl, Br, CN, and $NO_2$. In various embodiments, $A^1$ is substituted by F or CN. In some embodiments, $A^1$ is

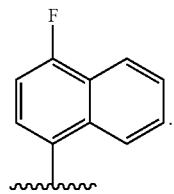 [SMILES: *c1ccc(F)c2ccccc12]

In various embodiments, $A^1$ is

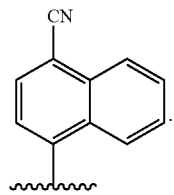

In various embodiments, a photocatalyst having the structure of Formula I is provided.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); Larock's Comprehensive Organic Transformations (VCH Publishers Inc., 1989), March, Advanced Organic Chemistry 4th Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such $\Phi_{ISC}$ losure). General methods for the preparation of compound as described herein are modified by the use of appropriate reagents and conditions, for the introduction of the various moieties found in the formula as provided herein.

Figure 2:
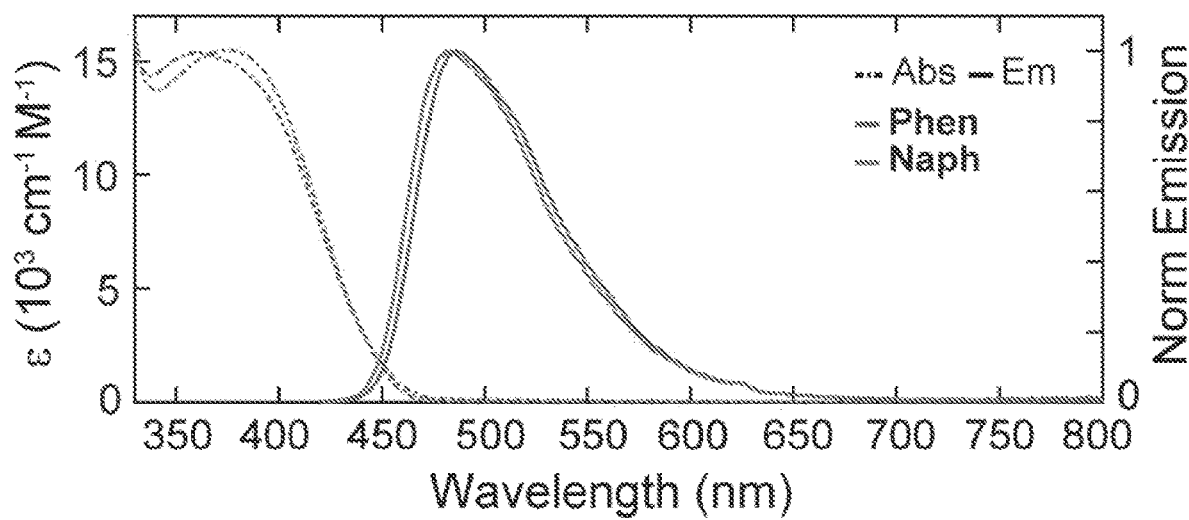
FIG. 2 shows steady-state absorption (dashed) and fluorescence (solid) of Phen and Naph in room-temperature (RT) dimethylacetamide (DMAc).

Compounds Phen and Naph (FIG. 1) were synthesized via a bromination of the 3,7 positions of the phenothiazine followed by a Suzuki reaction for core substitution and a Buchwald-Hartwig reaction for N-aryl substitution (see S.I. for details). FIG. 2 shows absorption spectra for Phen and Naph in DMAc. Both possess highly similar profiles with significant absorption in the visible region. The peak molar absorptivities ($\varepsilon$) of Phen and Naph were determined to be 15,400 $M^{-1}cm^{-1}$ (at 363 nm) and 15,500 $M^{-1}cm^{-1}$ (at 376 nm), respectively. While reasonably absorptive, the comparable values in the respective phenoxazine analogues are 24,000 and 25,900 $M^{-1}cm^{-1}$ (both at 388 nm). This variation with heteroatom may, without being bound by theory, originate in core chromophore structural differences and their impact on transition dipole moments. The phenoxazine core is nearly planar while the phenothiazine core is significantly bent, driven by the size and hybridization of the sulfur atom. Consistent with phenoxazine derivatives, the spectral similarity shared by Phen and Naph indicates that the N-aryl substituent minimally impacts the absorption of light.

Figure 10:
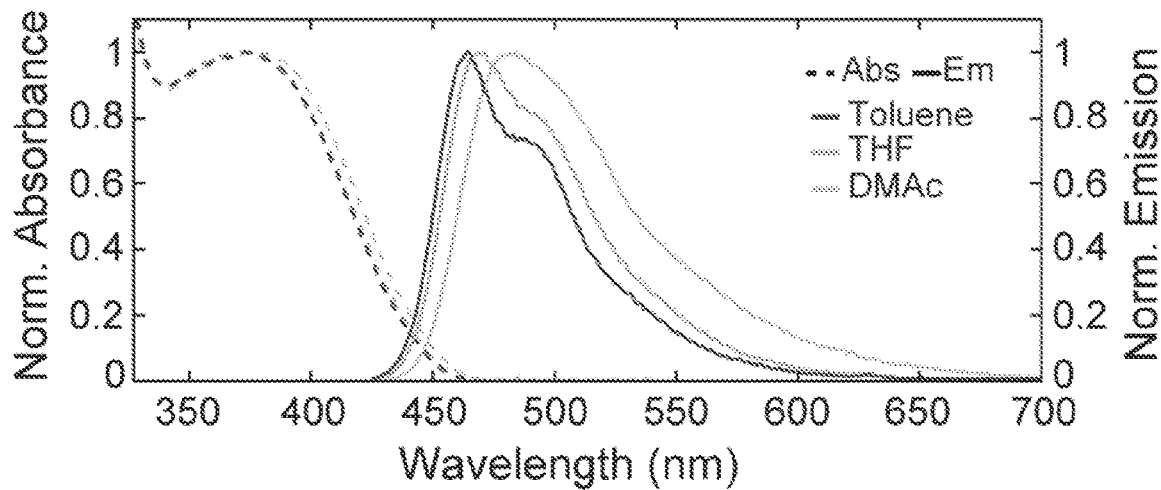
FIG. 10 shows absorbance and fluorescence spectra of Naph in DMAc, THF, and toluene at 20° C.

The fluorescence spectra of Phen and Naph in DMAc are also shown in FIG. 2. Due to competing phosphorescence, fluorescence was isolated by collecting data in the presence of oxygen. As with absorption, the fluorescence profiles are highly similar, indicating emitting singlets of comparable electronic character, which therefore do not involve the N-aryl substituent. Measurement of Naph fluorescence in multiple solvents reveals only modest solvatochromism (FIG. 10), highlighting a weakly polar emitting state. By the contrast of this emission behavior to that of well-characterized phenoxazine-containing analogues, we assign the state as being delocalized across the phenothiazine and both biphenyl substituents, which is accordingly denoted $S_{deloc}$. The formation of $S_{deloc}$ in Naph is a departure from the behavior of its direct phenoxazine analogue, in which the $S_1$ involves a CT from the phenoxazine core to the N-aryl substituent.

Due to the similarity of the oxidation potential between phenoxazine and phenothiazine analogues (Phen and Naph oxidize at 0.61 and 0.64 V vs SCE in DMAc, respectively (see SI for details), which is highly comparable to the corresponding values of 0.62 and 0.65 V for their respective phenoxazine analogues), the failure to form a CT state in Naph (characterized by reduction of the N-aryl substituent) is not attributed to CT destabilization. Rather, it indicates that the phenothiazine complexes possess a lower-lying core-localized $\pi^*$, which is consistent with the lower energy fluorescence of non-core-substituted phenothiazines relative to their phenoxazine analogues.

Figures 3A, 3B, 3C:
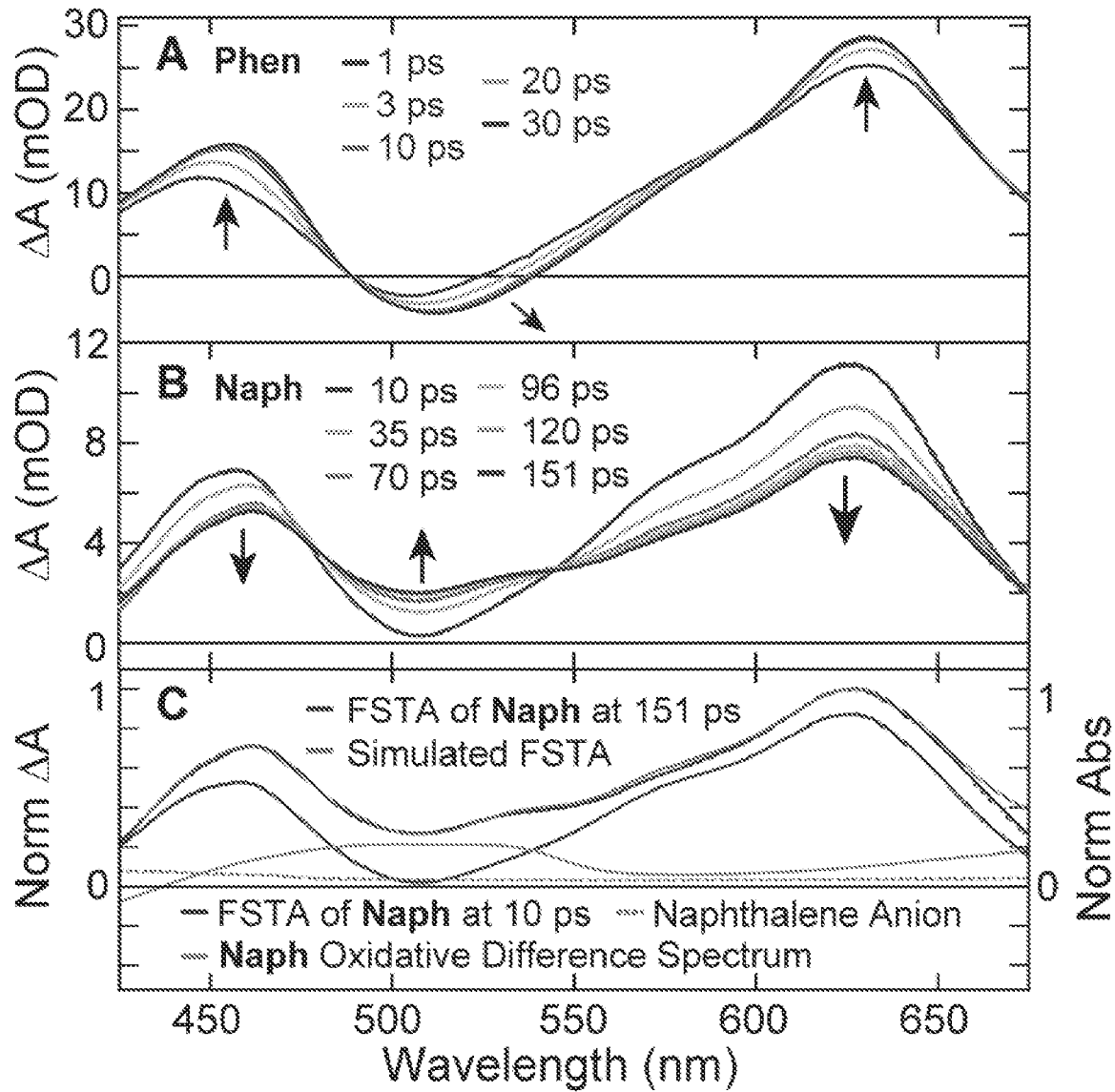
FIGS. 3A-3C show selected FSTA (femtosecond transient absorption) spectra for Phen (FIG. 3A) and Naph (FIG. 3B) in deaerated RT DMAc, with arrows to indicate the direction of dynamics.

However, despite the similarity of the Phen and Naph fluorescence profiles, their quantum yields of fluorescence ($\Phi_{fl}$) are substantially different at 0.41 and 0.17, respectively (Table 1). The lower $\Phi_{fl}$ for Naph hints at the possible co-population of a weakly emissive state (e.g., an orthogonal CT state), which may be masked by the more emissive $S_{deloc}$. Femtosecond transient absorption (FSTA) spectroscopy was used to study the difference between. FIGS. 3A-3C show spectra of Phen and Naph, in deaerated RT DMAc, following 400 nm excitation. Early dynamics for Phen (FIG. 3A) include the rise and sharpening of the peaks at 460 and 630 nm and are thus understood as cooling from the Franck-Condon state, likely consisting of vibrational and solvent relaxation. These changes are complete by 10 ps. Afterwards, the spectra decay monotonically with no shifting of features. Therefore, the spectrum at 10 ps is assigned to $S_{deloc}$.

Figure 16:
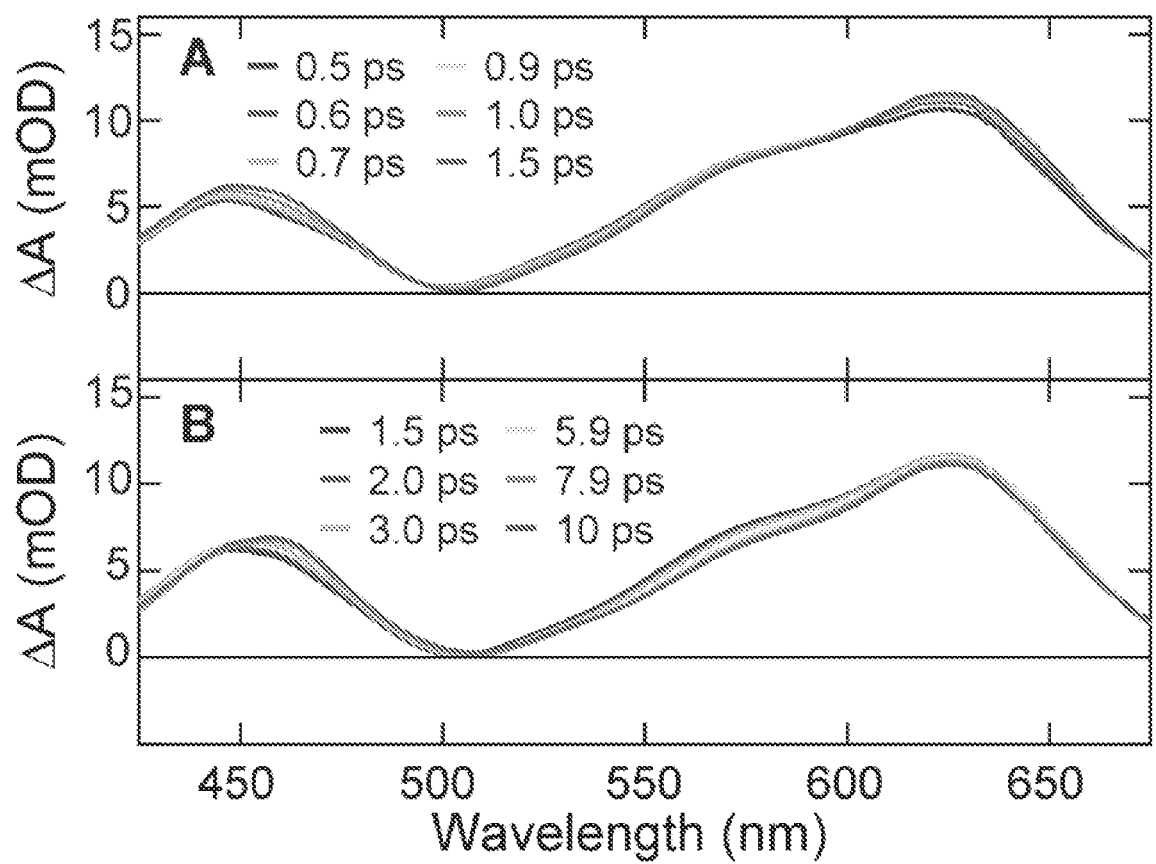
FIG. 16 shows early FSTA dynamics of Naph in RT DMAc.

Naph initially looks similar, with early times revealing comparable cooling dynamics (FIG. 16). However, these are then followed by significant spectral changes occurring with a 34 ps time constant, comprising of the loss of the peaks at 460 and 630 nm and a rise in intensity at ~500 nm, with associated isosbestic points at 480 and 550 nm (FIG. 3B). After these, spectral changes cease and all features decay monotonically on a timescale which cannot be resolved (>2 ns). While these data strongly indicate a 34 ps electronic interconversion away from $S_{deloc}$, the remaining peaks at 460 and 630 nm suggest that this does not proceed to completion. Rather, an equilibrium of excited states is established at late times (e.g., ~100 ps), which is consistent with fluorescence data (vide supra) which hinted at the partial formation of a weakly emissive CT state. Such a state in Naph would most likely consist of CT from the phenothiazine to the naphthyl group (so-called $S_{CT-Naph}$).

In order to probe for the presence of $S_{CT-Naph}$, the late-time FSTA spectrum is simulated using the absorption spectrum of anionic naphthalene, the oxidative difference spectrum of Naph generated by spectroelectrochemistry, and the early-time FSTA spectrum to account for the spectrum of the remaining $S_{deloc}$ (FIG. 3C). The resemblance of the simulated FSTA spectrum to the late-time FSTA data is remarkable and provides compelling evidence that the late-time FSTA spectrum represents a combination of $S_{CT-Naph}$ and $S_{deloc}$ and, further, that the phenothiazine donor and the naphthyl acceptor are electronically decoupled in the $S_{CT-Naph}$ state. Further, this modeling can be used to estimate the degree of interconversion from $S_{deloc}$ to $S_{CT-Naph}$, at ~50%, thus indicating that the two states are nearly isoenergetic.

Figures 4A, 4B, 4C:
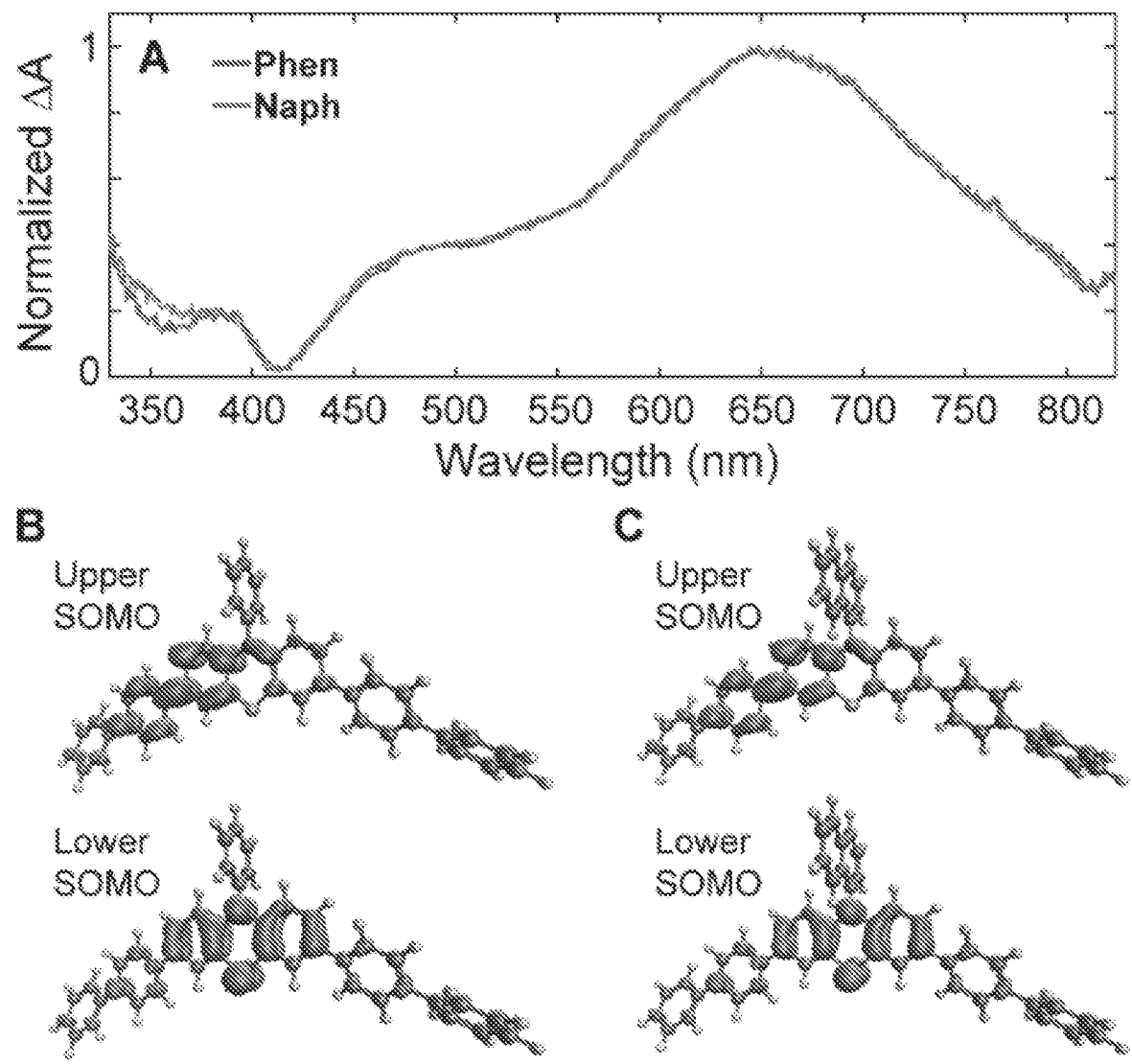
FIGS. 4A-4C show (FIG. 4A) triplet NSTA (nanosecond transient absorption) spectra of Phen and Naph in deaerated RT DMAc, taken at a time delay of 10 microseconds.

Nanosecond transient absorption was used (NSTA) to interrogate the long-lived lowest energy excited state. FIG. 4A shows the spectrum of Phen and Naph observed in deaerated RT DMAc 10 µs after 355 nm excitation. Each of these spectra are understood to originate from the lowest energy triplet excited state ($T_1$) due to the long observed lifetimes (>15 ms, as measured via phosphorescence experiments; see SI for more details) and high sensitivity of these lifetimes to oxygen. The similarity of the $T_1$ TA spectra of Phen and Naph indicates that both species possess a $T_1$ of comparable electronic character. DFT calculations reveal a $T_1$ characterized by a partial charge transfer from the phenothiazine core to a singlet core-biphenyl substituent (FIGS. 4B and 4C). We thus denote it in both compounds as $T_{CT-Biph}$. It is noted that the $\tau_{T_1}$ in both Phen and Naph is surprisingly and unexpectedly long for room-temperature solution phase compounds.

These lifetimes are more than 10 times longer than the phenoxazine analogues, which have electronically similar $T_1$ states ($T_{CT-Biph}$). As a consequence of this extended lifetime, phosphorescence, albeit weak, can be observed in solution at room temperature, which conveniently allows for experimental determination of $T_{CT-Biph}$ energy, $E_{00,T_1}$, by vibronic analysis of the phosphorescence spectra, which yields $E_{00,T_1}$=2.27 eV for both compounds. Notably $E_{00,T_1}$ is close to the DFT calculated triplet energy of 2.34 eV for both Phen and Naph, which was computed at the uM06/6-31+g(d,p)/CPCM-DMAc level of theory (CPCM solvation model of DMCA, N,N-dimethylacetamide).

As discussed above, there are differences in the yield of $T_1$ formation for both compounds with $\Phi_{ISC}$=0.76 and 0.41 for Naph and Phen, respectively. The higher triplet yield for the former is understood to be a result of occupation of the $S_{CT-Naph}$ state in the excited state equilibrium (vide supra): this CT state serves to both slow radiative decay and speed ISC. The latter effect is a consequence of the orthogonal π systems wherein the large change of angular momentum induced by the $S_{CT-Naph} \rightarrow T_{CT-Biph}$ transition facilitates spin-orbit coupling between the states. Without being bound by theory, it is believed that chemical modifications that selectively lower the energy of the $S_{CT-Naph}$ state should, in turn, cause $S_{CT-Naph}$ to form with unity (or near-unity) yield, thus leading to the aforementioned benefits to $\Phi_{ISC}$. Two new compounds were investigated that install electron withdrawing groups (EWGs) on the 4-position the naphthyl moiety. These are referred to as Fluoro-Naph and Cyano-Naph (FIG. 1). In the first case, the fluorine is a weak EWG due to competition between σ-withdrawing and π-donating character. In the second case, $S_{CT-Naph}$ is more significantly perturbed because the cyano substituent is both strongly σ- and π-withdrawing.

Figure 5:
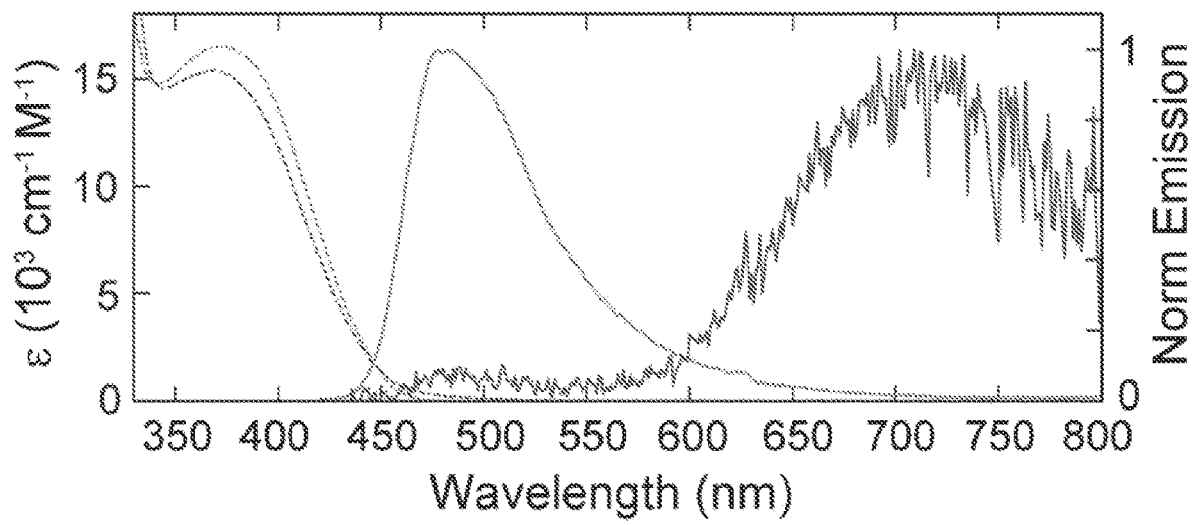
FIG. 5 shows steady-state absorption (dashed) and fluorescence (solid) of Fluoro-Naph and Cyano-Naph in RT DMAc. As with Phen and Naph, fluorescence spectra were collected under ambient air conditions to preclude emission from phosphorescence.

FIG. 5 shows absorption spectra for Fluoro-Naph and Cyano-Naph in DMAc. As was also seen in the comparison between Phen and Naph, the N-aryl substituent does not meaningfully impact the Franck-Condon state. The fluorescence data, however, tell a different story about the impact of the EWG. In Fluoro-Naph, the spectrum, shown in FIG. 5, is similar to that of Phen and Naph, although its $\Phi_{fl}$ of 0.034 is far weaker. The low $\Phi_{fl}$ suggests that fluorination has lowered the energy of the $S_{CT-Naph}$ state, thereby shifting the excited-state equilibrium away from the more highly emissive $S_{deloc}$ to the relatively dark $S_{CT-Naph}$. In Cyano-Naph, both spectral and quantum yield perturbations are more striking. We observe significant broadening and red shifting relative to the other three compounds and $\Phi_{fl}$ is extremely low, at 0.0008. These data suggest that Cyano-Naph has a substantially lowered $S_{CT-Naph}$ energy such that only emission from $S_{CT-Naph}$ is observed. In order to probe these assignments, we again turn to FSTA.

Figures 6A, 6B:
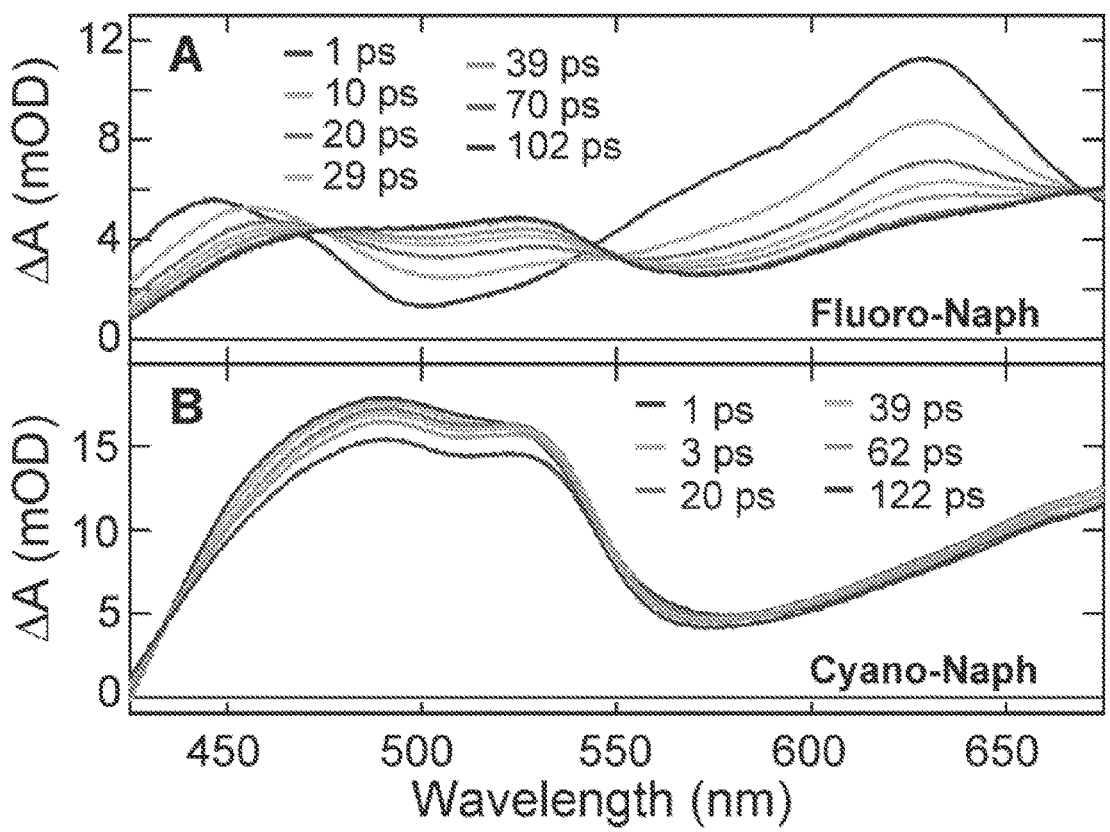
FIGS. 6A-6B show Selected FSTA spectra for Fluoro-Naph (A) and Cyano-Naph (B) in deaerated RT DMAc.

FIG. 6A shows FSTA spectra collected for Fluoro-Naph in deaerated RT DMAc, following 400 nm excitation. At early times (e.g., 1 ps), the data resemble those of Phen, indicating occupation of $S_{deloc}$. However, dramatic spectral evolution is then observed on a 19 ps timescale, resulting in the formation of a new feature centered at 500 nm. This later feature strongly resembles the modeled $S_{CT-Naph}$ state of Naph (vide supra) and is assigned accordingly. The fluorescence of Fluoro-Naph, then, originates from a small population of thermally accessible $S_{deloc}$. For Cyano-Naph (FIG. 6B), no significant spectral changes are observed, nor are any features present which resemble $S_{deloc}$. Rather, broad spectra centered around 500 nm are observed from the earliest time point, although subtle spectral changes consistent with cooling do occur. Given the similarity of the absorption profile of Cyano-Naph with the other compounds, and the assignment of the feature centered around 500 nm as originating from $S_{CT-Naph}$, it is inferred that $S_{deloc}$ is initially populated but that $S_{CT-Naph}$ is formed on an ultrafast timescale not resolved by these measurements.

Figures 7A, 7B, 7C:
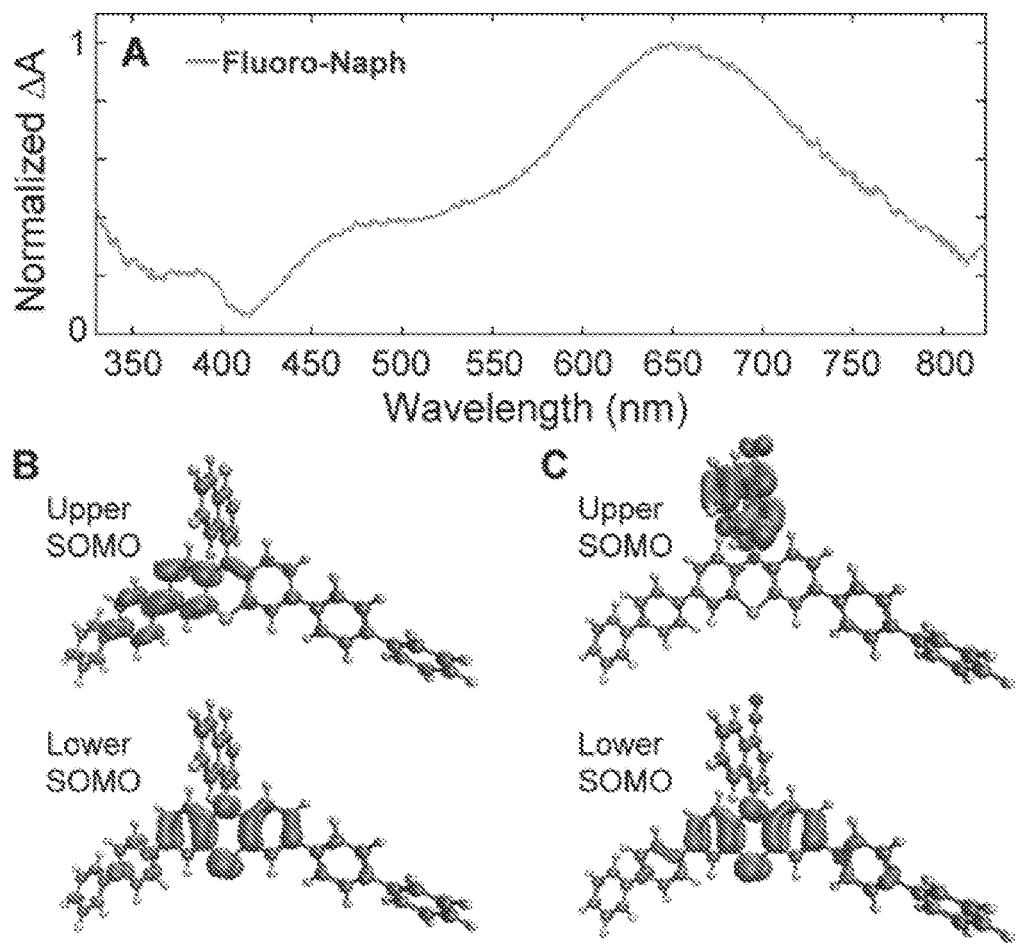
FIGS. 7A-7C show the (FIG. 7A) triplet NSTA spectrum of Fluoro-Naph in deaerated RT DMAc, taken at a time delay of 10 microseconds.

FIG. 7A shows the NSTA spectrum of Fluoro-Naph collected 10 µs after 355 nm excitation in deaerated RT DMAc. As with Phen and Naph, this is understood to originate from a triplet excited state due to the long lifetime (>15 ms) and its high sensitivity to oxygen. Given the spectral similarity with data from Phen and Naph (FIG. 4A), the $T_1$ of Fluoro-Naph is assigned as $T_{CT-Biph}$. Encouragingly, $\Phi_{ISC}$ of this species is measured to be near unity, at 0.96.

The compound Cyano-Naph, on the other hand, has a very low $\Phi_{ISC}$, such that measurement of the $T_1$ spectrum proved challenging. Attempts were made to form this state using tris[2-phenylpyridinato-$C^2$,N]iridium(III) (Ir(ppy)$_3$) as a triplet-triplet energy transfer (TTET) sensitizer, and indeed triplet quenching of Ir(ppy)$_3$ is observed using NSTA (Ir (ppy)$_3$ is used as the TTET sensitizer in the measurement of $\Phi_{ISC}$ for the other three compounds in this study as well). However, despite Ir(ppy)$_3$ having a sufficient $T_1$ energy for TTET, no Cyano-Naph triplet is observed after quenching. Without being bound by theory, this observation then suggests that the $T_1$ lifetime of Cyano-Naph is shorter than that of the sensitizer used (1.5 µs), thus preventing its accumulation. This observation is, in and of itself, important. The stark $T_1$ lifetime difference compared to what is seen in Phen, Naph, and Fluoro-Naph tells us that the state in Cyano-Naph are electronically different. We again turn to DFT for insight. The Cyano-Naph $T_1$ SOMOs (FIG. 7C) reveal substantive variations compared to what is seen for the other species (FIG. 7B and FIGS. 4B and 4C). Now, rather than $T_{CT-Biph}$, the $T_1$ in Cyano-Naph is clearly $T_{CT-Naph}$.

Both the change in the electronic character and the dramatic decrease in the yield of the $T_1$ arise due to the significant stabilization of the CT-Naph state in Cyano-Naph. The latter occurs by lowering the energy of $T_{CT-Naph}$ below that of $T_{CT-Biph}$. To understand the former, it is useful to examine the rate constants for the different pathways of depletion from $S_{CT-Naph}$ (radiative decay ($k_r$), non-radiative ground-state recovery ($k_{nr}$), and ISC ($k_{ISC}$) shown in Table 1. Relative to the other compounds, Cyano-Naph has a significantly higher $k_{nr}$ and, simultaneously, a much lower $k_{ISC}$, such that it could not be measured. Without being bound by theory, these effects can be understood in the following way: First, $k_{ISC}$ is slower because the nature of the $T_1$ is changed. Cyano-Naph undergoes a fundamentally different ISC process than the other compounds in this study, namely, $S_{CT-Naph} \rightarrow T_{CT-Naph}$ rather than the substantial electron density shifting $S_{CT-Naph} \rightarrow T_{CT-Biph}$. This new pathway has low driving force and no longer has the advantages of enhanced spin-orbit coupling afforded to the other pathway. Second, the substantial increase in $k_{nr}$ is attributed to the Energy Gap Law. We can still presume that $S_{CT-Naph}$ lies in the Marcus Inverted region relative to the ground state, but it is now much less so compared to the other compounds in this study, thereby lowering the thermodynamic barrier for non-radiative decay. Combined, these effects on $k_{nr}$ and $k_{ISC}$ result in extremely low $\Phi_{ISC}$ for Cyano-Naph.

Lastly, considering the question kinetic differences in ISC between phenothiazine compounds and their phenoxazine analogues, we observe that Phen, Naph, and Fluoro-Naph have $k_{ISC}$ values roughly comparable to phenoxazine analogues with $S_1$ states of similar electronic character (see SI for more details). Interestingly, this similarity in $k_{ISC}$ is despite the lower driving force for the phenothiazine complexes that result from the lower-energy $S_{deloc}$ and $S_{CT-Naph}$ states in these sulfur-containing species. Without being bound by theory, these results may indicate that there is higher spin-orbit coupling for the phenothiazine complexes arising from the heavy atom effect but that competing effects obviate this spin-orbit coupling advantage.

Figure 8:
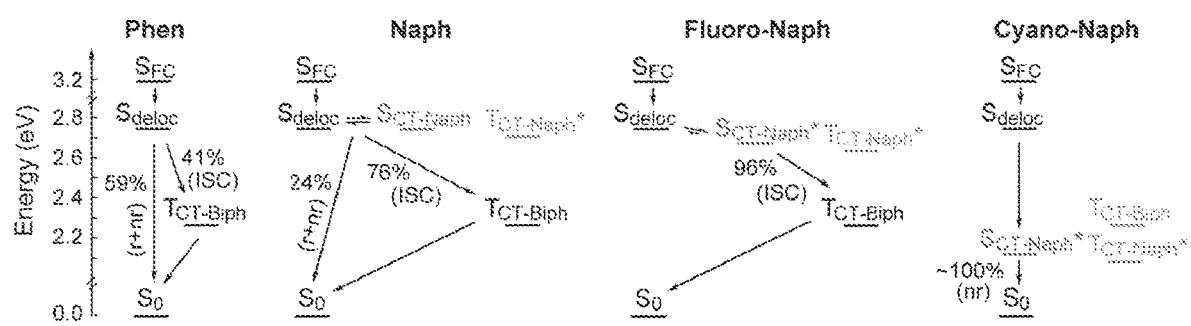
FIG. 8 shows energy-level diagrams of the compounds studied. The $S_{CT-Naph}$ state is highlighted in red, and the color grey indicates triplet states that are not populated. Only pathways that describe at least 10% of excited-state population decay are shown. * indicates that the energy of a given state is approximate and not intended to have quantitative accuracy. The energies of all other states originate from absorption or emission $E_{00}$ energies.

FIG. 8 shows a summarizing energy-level diagram of all four species studied here. We find that for Phen, the lowest energy singlet is $S_{deloc}$, a state whose high $k_r$ competes effectively against $k_{ISC}$, resulting in a relatively low $\Phi_{ISC}$. Naph introduces a nearly isoenergetic singlet charge transfer state ($S_{CT-Naph}$) as an equilibrium partner. Within this state, the donor versus acceptor orthogonality lowers $k_r$ while simultaneously increasing $k_{ISC}$ towards a triplet characterized by charge transfer from the phenothiazine to a biphenyl arm ($T_{CT-Biph}$). Fluoro-Naph, by virtue of inclusion of an EWG, exhibits an excited-state equilibrium that is shifted significantly towards $S_{CT-Naph}$, ultimately resulting in a near-unity $\Phi_{ISC}$. Interestingly, lowering the CT-Naph energy further in Cyano-Naph does not have the effect of increasing $\Phi_{ISC}$ that was desired at the outset but rather results in fast and efficient non-radiative ground-state recovery. In essence $S_{CT-Naph}$ has been lowered too much, speeding $k_{nr}$ and taking away needed driving force for SOCT-ISC to the $T_{CT-Biph}$.

More broadly, we have demonstrated that phenothiazine compounds, Fluoro-Naph, in particular, can be designed to have comparable properties as the leading phenoxazine photocatalysts. These properties include the absorption of visible light, highly negative excited state reduction poten-

TABLE 1

Photophysical Parameters of Compounds in this Study

| | $\tau_{singlet}{}^a$ (ns) | $\Phi_{fl}$ | $\Phi_{ISC}$ | $E^{0*}{}_{T1}{}^b$ (V vs SCE) | $k_r{}^{c,d}$ (s$^{-1}$) | $k_{ISC}{}^c$ (s$^{-1}$) | $k_{nr}{}^{c,d}$ (s$^{-1}$) |
|---|---|---|---|---|---|---|---|
| Phen | 4.03 ± 0.01 | 0.41 ± 0.04 | 0.41 ± 0.06 | −1.66 | 1.0 × 10$^8$ ± 1 × 10$^7$ | 1.0 × 10$^8$ ± 1 × 10$^7$ | 5 × 10$^7$ ± 2 × 10$^7$ |
| Naph | 3.79 ± 0.03 | 0.17 ± 0.01 | 0.76 ± 0.10 | −1.63 | 4.5 × 10$^7$ ± 2 × 10$^6$ | 2.0 × 10$^8$ ± 3 × 10$^7$ | 2 × 10$^7$ ± 3 × 10$^7$ |
| Fluoro-Naph | 5.41 ± 0.02 | 0.034 ± 0.003 | 0.96 ± 0.14 | −1.61 | 6.3 × 10$^6$ ± 5 × 10$^5$ | 1.8 × 10$^8$ ± 3 × 10$^7$ | 8 × 10$^5$ ± 3 × 10$^7$ |
| Cyano-Naph | 1.33 ± 0.07 | 8 × 10$^{-4}$ ± 1 × 10$^{-4}$ | — | — | 6 × 10$^5$ ± 1 × 10$^5$ | | 7.5 × 10$^8$ |

$^a\tau_{singlet}$ is measured using time-correlated single photon counting, using 402 nm excitation in deaerated DMAc.
$^b$Potential of oxidation of the $T_1$, determined by the potential of oxidation of the ground-state compound (Table 4) minus $E_{00,T1}$ (Table 3).
$^c$Rate constants are calculated using the following equations: $kr = \Phi_{fl}/\tau_{singlet}$, $k_{ISC} = \Phi_{ISC}/\tau_{singlet}$ and $k_{nr} = \tau_{singlet}^{-1} - k_r - k_{ISC}$.
$^d$These values refer exclusively to $S_1 \rightarrow$ ground-state pathways.

tials (see Table 1), and, in the case of Fluoro-Naph, a high $\Phi_{ISC}$ (with even longer triplet lifetimes). There are impactful differences in the excited state behavior of phenothiazine complexes which must be accounted for in order to ensure a high $\Phi_{ISC}$ via a CT-mediated mechanism. One important difference is a lower-energy $S_{deloc}$ state in the phenothiazine compounds, which suggests a lowering of the CT state (relative to phenoxazine analogues) in order to ensure efficient CT formation. We have found that, while it is important to stabilize the CT state below competing states, one should be cautious to not lower the CT energy by too much, as doing so can result in a lower $k_{ISC}$ and a larger $k_{nr}$. For most efficient CT-mediated ISC, a general strategy would be to lower the energy of the CT state as little as possible while still achieving ~100% yield of CT formation in the singlet manifold. However, the effect of solvent polarity must also be taken into account, as low polarity solvents preferentially destabilize CT states relative to non-polar excited states and high polarity solvents can significantly lower the energy of CT states below what is optimal for ISC.

Methods of Using

In various embodiments, a method of polymerizing a substrate with a compound of Formula I is provided. The method includes: providing a composition comprising at least one polymerizable monomer and at least one compound of Formula I; and irradiating the composition with electromagnetic radiation, wherein the composition is free from metals. The compound of Formula I can be present in a catalytic amount, such as about 0.01 to about 40% (w/w). In various embodiments, the compound of Formula I is present in an amount of about 0.01, 0.05, 0.1, 0.2, 0.3, 0.4, 0.5, 0.6, 0.7, 0.8, 0.9, 1, 2, 3, 4, 5, 6, 7, 8, 9 10, 15, 20, 25, 30, 35, or 40% (w/w) relative to the amount of monomer.

Suitable monomers include, but are not limited to, acrylates, styrene, acrylamides, acrylonitrile, vinyl chloride, methylacrylonitrile, vinyl acetate, and acrylic acid, and other vinyl-containing monomers. In some embodiments, the monomer comprises methyl acrylate (MA), methyl methacrylate (MMA), or a mixture thereof. The composition can include a mixture of monomers, and each monomer can be from about 0.1 to about 99% (w/w) of the composition. The electromagnetic radiation can be UV or visible light, including light from light-emitting diode sources (LED) such as white LEDs. In various embodiments, the electromagnetic radiation has a wavelength of about 250 nm to about 800 nm, or about 250, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 nm. The composition can optionally further include a radical initiator, such as an aryl sulfonyl halide, including aryl sulfonyl chlorides and aryl sulfonyl bromides. In one embodiment, the radical initiator is phenyl sulfonyl chloride or phenyl sulfonyl bromide. The radical initiator can be present in an amount of about 0.01 to about 40% (w/w). In various embodiments, the radical initiation is present in an amount of about 0.01, 0.05, 0.1, 0.2, 0.3, 0.4, 0.5, 0.6, 0.7, 0.8, 0.9, 1, 2, 3, 4, 5, 6, 7, 8, 9 10, 15, 20, 25, 30, 35, or 40% (w/w) relative to the amount of monomer.

As used herein, the term "free from metals" means that that composition contains no measurable amount of metal or that the metal content is sufficiently low that it has no catalytic or other effect on the polymerization of the monomer composition. The term "metal" as used herein means a metal that can affect the course of the polymerization reaction in either a catalytic or a stoichiometric manner. Typical metals that can affect polymerization reaction and which the compositions described herein are free from include transition metals such as copper, zinc, platinum, palladium, ruthenium, iridium, zirconium, and the like.

The reaction can be carried out in a suitable solvent, include a ketone-based solvent. Suitable ketone-based solvents include, but are not limited to acetone, methyl isobutyl ketone, and the like.

The compounds of Formula I are also suitable for use in other photocatalyzed transformations or photoredox catalysis. Compounds of Formula I can be used in small molecule reactions, such as cross-coupling, atom transfer radical addition (ATRA), and radical addition and radical substitution. In some embodiments, a photocatalyzed transformation with a compound of Formula I optionally uses a suitable transition metal catalyst.

In various embodiments, a method of photocatalytically transforming a substrate with a compound of Formula I is provided. The method includes: providing a composition that includes at least one substrate capable of undergoing a photochemical transformation and at least one compound of Formula I; and irradiating the composition with electromagnetic radiation. In various embodiments, a method of photocatalytically cross-coupling a substrate in the presence of a compound of Formula I is provided. The method includes: providing a composition that includes at least one substrate capable of undergoing a photochemical transformation and cross-coupling with at least one second substrate, and at least one compound of Formula I; and irradiating the composition with electromagnetic radiation. In various embodiments, the first and second substrates can be the same or different. Examples of cross-coupling reactions include, without limitation, the cross-coupling of a primary amine and an alkyl ammonium.

In various embodiments, a method of photocatalytically reacting a substrate via ATRA in the presence of a compound of Formula I is provided. The method includes: providing a composition that includes at least one substrate capable of photochemically undergoing an ATRA with at least one second substrate, and at least one compound of Formula I; and irradiating the composition with electromagnetic radiation. In various embodiments, the first and second substrates can be the same or different. Example substrates that can be used in an ATRA reaction include, without limitation, methyl methacrylate.

In various embodiments, a method of free radical addition or free radical substitution by photocatalytically reacting a substrate in the presence of a compound of Formula I is provided. The method includes: providing a composition that includes at least one substrate capable of undergoing a free radical addition or free radical substitution with at least one second substrate, and at least one compound of Formula I; and irradiating the composition with electromagnetic radiation. In various embodiments, the first and second substrates can be the same or different.

In some embodiments, the methods described herein can optionally include at least one transition metal catalyst, and can include any of the amounts of compound of Formula I described herein, as well as any of the wavelengths of electromagnetic radiation described herein. Suitable transition metal catalysts include, without limitation, organic complexes of Pd, Ru, Rh, Cu, Ni, Fe, and the like, that are known to be useful in photocatalytic transformations.

Suitable substrates include $C_{1-30}$ alkanes, $C_{2-30}$ alkenes, $C_{2-30}$ alkynes, $C_{5-22}$ aryl, $C_{5-22}$ heteroaryl, $C_{3-30}$ cycloalkyl, $C_{3-30}$ heterocyclyl, and combinations thereof, wherein each substrate is optionally substituted by at least one group selected from the group consisting of F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein each occurrence of R is independently hydrogen or C$_{1-10}$ alkyl. In various embodiments, at least one carbon atom in an all-carbon substrate can be replaced with a heteroatom, such as N, O, S, P, or Si. Thus, by way of example, a substrate that is a C$_5$ alkane can have a carbon atom (along with the corresponding hydrogen atoms) replaced by an O (oxygen) atom to be an ether substrate. Cyclic substrates can be substituted within the ring by any of the substituents described therein and that results in an isolatable compound such that, for example, the at least one substrate can be a lactone, lactam, and the like.

In various embodiments, any suitable reagent or solvent that is compatible with the reaction conditions necessary to perform the methods described herein can be used.

EXAMPLES

Various embodiments of the present application can be better understood by reference to the following Examples which are offered by way of illustration. The scope of the present application is not limited to the Examples given herein.

Synthesis of Phenothiazine Compounds

Materials and Methods

General:

All reagents were purchased from commercial suppliers and used without any further purification. Acetic acid (certified ACS), chloroform (ACS reagent), BHT stabilized tetrahydrofuran (ACS reagent), dichloromethane (ACS reagent), methanol (ACS reagent), hexanes (ACS reagent), and ethyl acetate (ACS reagent) were purchased from Fischer. Unstabilized tetrahydrofuran and toluene were purified using an mBraun MB-SPS-800 solvent purification system and kept under nitrogen atmosphere. Anhydrous MgSO$_4$ and Na$_2$SO$_4$ were purchased from Fischer.

Instruments for Compound Characterization

Nuclear magnetic resonance spectra were recorded on a Bruker 400 MHz NMR Spectrometer. All $^1$H NMR experiments are reported in δ units, parts per million (ppm), and were measured relative to the signals for residual chloroform (7.26 ppm) benzene (7.15 ppm) or dimethylsulfoxide (2.50 ppm) in deuterated solvent. All $^{13}$C NMR spectra are reported in ppm relative to d-DMSO (39.52 ppm) or benzene-d$_6$ (128.62 ppm). Electrospray Ionization Mass Spectroscopy (ESI-MS) and Atmospheric Pressure Chemical Ionization Mass Spectroscopy (APCI-MS) were performed by the Colorado State University Central Instrumentation Facility.

Procedures and Characterization

General Synthetic Scheme for "Naph", "Fluoro-Naph", and "Cyano-Naph"

Buchwald Coupling

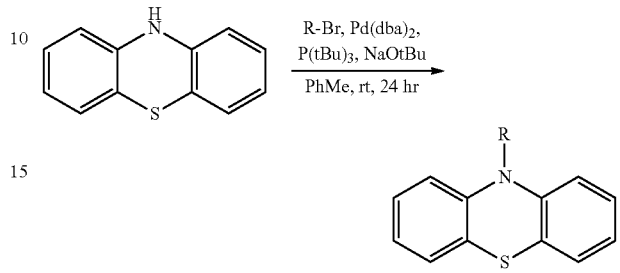

Phenothiazine, 4-bromo-1-naphthonitrile, 1-bromonaphthalene, sodium tert-butoxide (NaO$^t$Bu), tri-tert-butylphosphine (P($^t$Bu)$_3$), and palladium dibenzylideneacetone (Pd(dba)$_2$) were purchased from Sigma Aldrich. Bromobenzene and 1-bromo-4-fluoronaphthalene were purchased from TCI.

Bromination

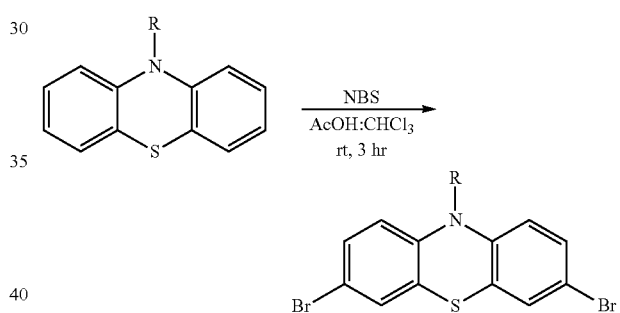

N-Bromosuccinamide (NBS) and phenothiazine were purchased from Sigma Aldrich.

Suzuki Coupling

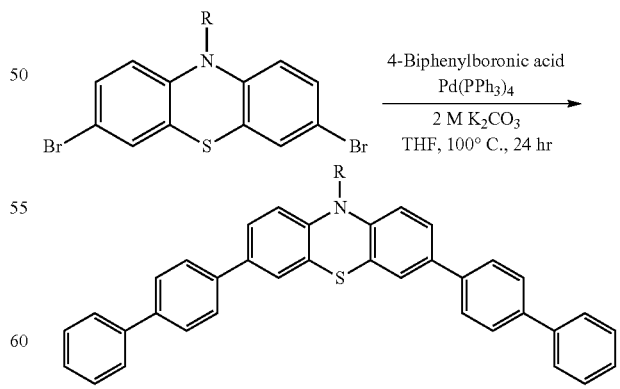

Potassium carbonate (K$_2$CO$_3$) was purchased from Fischer. Tetrakis(triphenylphosphine)palladium(0) (Pd(PPh$_3$)$_4$) was purchased from Sigma Aldrich. 4-Biphenylboronic acid was purchased from Oxchem.

Synthesis of Naph

Synthesis of 10-(Naphthalen-1-yl)-10H-Phenothiazine

Phenothiazine (0.996 g, 5.00 mmol, 1.00 eq.) and NaO$^t$Bu (0.720 g, 7.50 mmol, 1.50 eq.) were added to a flame-dried storage tube, cycled 3× with $N_2$ and vacuum, and brought into an $N_2$-filled glovebox. Pd(dba)$_2$ (28.8 mg, 50.0 μmol %, 1.00 mol %), 1 M P(tBu)$_3$ in toluene (40.0 μL, 40.0 μmol, 0.800 mol %) and 7.5 mL toluene were added and the storage tube was brought out of the glove box. Sparged 1-bromonaphthalene (0.770 mL, 5.50 mmol, 1.10 eq) was added and the reaction mixture was heated at 60° C. for 24 hours. The reaction mixture was diluted with EtOAc, transferred to a separatory funnel and washed with $H_2O$ and brine. The organic layer was dried over $Na_2SO_4$, concentrated and sublimed at 150° C. yielding the desired product as an off white solid (1.03 g, 63% yield). The NMR matched that previously reported.

Synthesis of 3,7-Dibromo-10-(Naphthalen-1-yl)-10H-Phenothiazine

In a 250 mL round bottom flask, charged with a stir bar and wrapped in foil, 10-(naphthalen-1-yl)-10H-phenothiazine (0.651 g, 2.00 mmol, 1.00 eq.) was dissolved in 60 mL 1:1 AcOH:CHCl$_3$. N-Bromosuccinimide (0.748 g, 4.20 mmol, 2.10 eq.) was added portion wise over 10 minutes and the reaction was stirred for 2 hours. The reaction mixture was concentrated under vacuum, re-dissolved in DCM, washed with $H_2O$ and brine and the organic layer was dried over $Na_2SO_4$. The crude mixture was concentrated until solid began precipitating and minimal DCM was added until the solution became homogeneous. MeOH was layered on top of this solution and the flask was put in a −25° C. freezer. The recrystallization was filtered, yielding the desired product as a slightly red solid (0.622 g, 64% yield). $^1$H NMR (400 MHz, DMSO-d$_6$) δ 8.15 (dd, J=17.7, 7.9 Hz, 2H), 7.90 (d, J=8.4 Hz, 1H), 7.81-7.74 (m, 2H), 7.64-7.55 (m, 2H), 7.32 (d, J=2.4 Hz, 2H), 6.97 (dd, J=8.9, 2.4 Hz, 2H), 5.83 (d, J=8.8 Hz, 2H). $^{13}$C NMR (101 MHz, DMSO-d$_6$) δ 142.07, 135.25, 130.15, 129.86, 129.64, 129.56, 129.12, 128.42, 127.88, 127.09, 126.99, 122.20, 120.59, 117.11, 114.15. HRMS (ESI): calculated for M+ $C_{22}H_{13}Br_2NS$, 480.9135; observed 480.9111.

Synthesis of 3,7-Di([1,1'-Biphenyl]-4-yl)-10-(Naphthalen-1-yl)-10H-Phenothiazine (Naph)

3,7-Dibromo-10-(naphthalen-1-yl)-10H-phenothiazine (0.232 g, 0.480 mmol, 1.00 eq.) and 4-biphenylboronic acid (0.382 g, 1.90 mmol, 4.00 eq.) were added to a flame dried 200 mL schlenk flask equipped with a reflux condenser. 20 mL THF and 6 mL sparged 2 M $K_2CO_3$ were added, followed by Pd(PPh$_3$)$_4$ (93.0 mg, 72.0 μmol, 15.0 mol %). The reaction was heated to 100° C. for 24 hours, concentrated under vacuum, dissolved in DCM, and washed with $H_2O$ and brine. The organics were dried with MgSO$_4$, concentrated under reduced pressure and purified by flash chromatography (1:4 DCM:Hexanes, R$_f$=0.15) followed by a recrystallization from DCM/MeOH yielding the product as a bright yellow solid (0.230 mg, 76% yield). $^1$H NMR (400 MHz, DMSO-d$_6$) δ 8.22 (dd, J=6.5, 2.8 Hz, 1H), 8.17 (d, J=7.4 Hz, 1H), 8.03 (d, J=8.0 Hz, 1H), 7.89-7.80 (m, 2H), 7.74-7.56 (m, 14H), 7.52-7.42 (m, 6H), 7.41-7.32 (m, 2H), 7.19 (dd, J=8.7, 2.2 Hz, 2H), 6.02 (d, J=8.6 Hz, 2H). $^{13}$C NMR (101 MHz, Benzene-d$_6$) δ 143.36, 141.31, 140.24, 139.04, 137.75, 135.92, 135.65, 132.05, 129.58, 129.34, 129.11, 129.08, 127.50, 127.36, 127.20, 127.01, 125.94, 125.38, 124.25, 120.43, 116.68 (Note that signal to noise was low due to poor solubility). HRMS (APCI): calculated for M+H $C_{46}H_{31}NS$, 630.2255; observed 630.2266.

Synthesis of Fluoro-Naph

Synthesis of 10-(4-Fluoronaphthalen-1-yl)-10H-Phenothiazine

1-Bromo-4-fluoronaphthalene (2.50 g, 11.1 mmol, 2.00 eq.), phenothiazine (1.11 g, 5.55 mmol, 1.00 eq.) and NaO$^t$Bu (1.07 g, 11.1 mmol, 2.00 eq.) were weighed into 20 mL scintillation vials, brought into an $N_2$ filled glovebox and added to a flame-dried storage tube. Pd(dba)$_2$ (63.8 mg, 0.111 mmol, 2.00 mol %), 1 M P($^t$Bu)$_3$ in toluene (0.160 mL, 0.167 mmol, 3.00 mol %) and 15 mL toluene were added to the storage tube. The reaction was brought out of the glovebox, heated to 60° C. for 24 hours, exposed to air, and concentrated to dryness. The crude reaction mixture was re-dissolved in DCM and washed with $H_2O$ and brine. The organics were dried over MgSO$_4$, concentrated to minimal solvent and passed through a silica plug (washing with 8:1 hexanes:EtOAc). This was concentrated and cold MeOH was added. The crashed out solid was collected by filtration yielding the target compound as a slightly yellow solid (0.975 g, 51% yield). $^1$H NMR (400 MHz, Benzene-d$_6$) δ 8.06 (d, J=8.4 Hz, 1H), 7.96 (d, J=8.5 Hz, 1H), 7.09 (t, J=7.6 Hz, 1H), 7.02-6.88 (m, 4H), 6.77 (dd, J=10.1, 8.1 Hz, 1H), 6.55 (td, J=7.4, 1.3 Hz, 2H), 6.47 (td, J=7.8, 7.4, 1.6 Hz, 2H), 5.96 (dd, J=8.2, 1.2 Hz, 2H). $^{13}$C NMR (101 MHz, Benzene-d$_6$) δ 160.01, 157.48, 144.33, 133.56, 133.52, 133.23, 133.17, 129.84, 129.75, 128.54, 127.37, 127.35, 127.26, 127.05, 127.05, 125.74, 125.56, 124.27, 124.25, 122.99, 121.58, 121.53, 120.39, 116.18, 110.57, 110.36. $^{19}$F NMR (376 MHz, Benzene-d$_6$) δ −120.77. HRMS (ESI): calculated for M+ $C_{22}H_{14}FNS$, 343.0831; observed 343.0832.

Synthesis of 3,7-Dibromo-10-(4-Fluoronaphthalen-1-yl)-10H-Phenothiazine

In a 250 mL round bottom flask wrapped in foil, 10-(4-Fluoronaphthalen-1-yl)-10H-Phenothiazine (0.687 g, 2.00 mmol, 1.00 eq.) was dissolved in 60.0 mL 1:1 AcOH:CHCl$_3$. NBS (0.748 g, 4.20 mmol, 2.10 eq.) was added portion-wise over the course of 20 minutes. The reaction was stirred for 3 hours, quenched with saturated NaHCO$_3$, and the aqueous layer was extracted with DCM. The combined organics were washed with $H_2O$ and brine, dried over $Na_2SO_4$, and concentrated under reduced pressure. Recrystallization from DCM:MeOH at −25° C. yielded the target compound as a white solid (0.711 g, 71% yield). $^1$H NMR (400 MHz, Benzene-d$_6$) δ 8.04 (d, J=8.2 Hz, 1H), 7.77 (d, J=8.3 Hz, 1H), 7.13-7.01 (m, 2H), 6.96 (d, J=2.3 Hz, 2H), 6.73 (d, J=7.4 Hz, 2H), 6.53 (dd, J=8.8, 2.3 Hz, 2H), 5.55 (d, J=8.8 Hz, 2H). $^{13}$C NMR (101 MHz, Benzene-d$_6$) δ 160.16, 157.62, 132.53, 132.47, 132.47 130.13, 129.50, 129.41, 129.24, 128.76, 127.61, 127.59, 125.78, 125.61 123.64, 123.61, 121.87, 121.79, 121.74, 117.24, 115.39, 110.58, 110.37. $^{19}$F NMR (376 MHz, C$_6$D$_6$) δ −119.74. HRMS (ESI): calculated for M+2 (most abundant isotope) C$_{22}$H$_{12}$Br$_2$FNS, 500.9021; observed 500.9008.

Synthesis of 3,7-Di([1,1'-Biphenyl]-4-yl)-10-(4-Fluoronaphthalen-1-yl)-10H-Phenothiazine (Fluoro-Naph)

3,7-Dibromo-10-(4-fluoronaphthalen-1-yl)-10H-phenothiazine (0.501 g, 1.00 mmol, 1.00 eq.) and 4-biphenylboronic acid (0.792 g, 4.00 mmol, 4.00 eq) were added to a 250 mL storage tube. After cycling the tube with N$_2$ and vacuum three times, the storage tube was taken into a nitrogen filled glove box. Pd(PPh$_3$)$_4$ (58.0 mg, 50.0 µmol, 5.00 mol %) was added to the storage tube and the mixture was dissolved in 20 mL THF. The storage tube was removed from the glove box and 10 mL of sparged 2 M K$_2$CO$_3$ was added. The resultant heterogeneous mixture was heated for 24 hours at 100° C. After the reaction was complete, the mixture was cooled to room temperature, exposed to oxygen, concentrated under reduced pressure and transferred to a separatory funnel, rinsing with DCM. The aqueous layer was extracted twice with DCM. The combined organics were washed with H$_2$O, brine, dried with Na$_2$SO$_4$ and concentrated under reduced pressure. The resultant solid was dissolved in toluene, passed through a silica plug and again concentrated under reduced pressure. Recrystallization from DCM:MeOH at −25° C. yielded the desired product as a yellow solid (0.550 g, 85% yield). $^1$H NMR (400 MHz, Benzene-d$_6$) δ 8.12 (dd, J=14.0, 8.3 Hz, 2H), 7.62-7.43 (m, 10H), 7.37 (d, J=8.3 Hz, 4H), 7.25 (t, J=7.6 Hz, 4H), 7.18 (s, 2H), 7.15-7.05 (m, 3H), 6.92-6.83 (m, 3H), 6.06 (d, J=8.5 Hz, 2H). $^{13}$C NMR (101 MHz, Benzene-d$_6$) δ 143.31, 141.26, 140.36, 138.95, 135.86, 133.48, 133.44, 129.79, 129.70, 129.14, 128.75, 128.70, 127.92, 127.55, 127.36, 127.04, 125.95, 125.47, 124.27, 124.24, 121.78, 121.74, 120.61, 116.57, 110.77, 110.55 (Note that signal to noise was low due to poor solubility). $^{19}$F NMR (376 MHz, C$_6$D$_6$) δ-120.27. HRMS (ESI): calculated for M+K C$_{46}$H$_{30}$FNS, 686.1715; observed 686.1878.

Synthesis of Cyano-Naph

Synthesis of 4-(10H-Phenothiazin-10-yl)-1-Naphthonitrile

4-Bromo-1-naphthonitrile (1.28 g, 5.50 mmol, 1.10 eq.), phenothiazine (0.996 g, 5.00 mmol, 1.00 eq.) and NaO$^t$Bu (0.720 g, 7.50 mmol, 1.50 eq.) were added to a flame-dried 100 mL storage tube and brought into an N$_2$ filled glovebox. Pd(dba)$_2$ (29.0 mg, 50.0 µmol, 2.00 mol %), 1 M P($^t$Bu)$_3$ in toluene (40.0 µL, 40.0 µmol, 0.800 mol %) and 15 mL toluene were added to the storage tube. The reaction was brought out of the glovebox, heated to 50° C. for 24 hours, exposed to air, and concentrated to dryness. The crude reaction mixture was re-dissolved in DCM and washed with H$_2$O then brine and the organics were dried over Na$_2$SO$_4$. This was concentrated to minimal solvent layered with MeOH and put in a −25° C. freezer to recrystallize. The crystals that formed were collected by filtration, yielding the target compound as an orange solid (1.41 g, 81% yield). $^1$H NMR (400 MHz, DMSO-d6) δ 8.46 (d, J=7.6 Hz, 1H), 8.29 (d, J=8.3 Hz, 1H), 8.16 (d, J=8.4 Hz, 1H), 8.00 (d, J=7.6 Hz, 1H), 7.89 (ddd, J=8.3, 6.9, 1.2 Hz, 1H), 7.75 (ddd, J=8.2, 6.9, 1.1 Hz, 1H), 7.13 (dd, J=7.4, 1.8 Hz, 2H), 6.91-6.78 (m, 4H), 6.03 (d, J=7.9, 1.4 Hz, 2H). $^{13}$C NMR (101 MHz, DMSO-d$_6$) δ 142.59, 141.19, 134.36, 133.96, 130.55, 130.31, 129.33, 127.51, 126.78, 123.62, 123.20, 119.13, 117.16, 115.70, 110.04. HRMS (ESI): calculated for M+ C$_{23}$H$_{14}$N$_2$S, 350.0878; observed 350.0883.

Synthesis of 4-(3,7-Dibromo-10H-Phenothiazin-10-yl)-1-Naphthonitrile

To a 250 mL round bottom flask wrapped in foil, 4-(10H-phenothiazin-10-yl)-1-naphthonitrile (0.700 g, 2.00 mmol, 1.00 eq.) was dissolved in 60 mL 1:1 AcOH:CHCl$_3$. NBS (0.743 g, 4.20 mmol, 2.10 eq.) was added portion-wise over the course of 20 minutes. The reaction was stirred for 3 hours and the reaction mixture was concentrated to dryness. The crude mixture was re-dissolved in DCM and washed with H$_2$O and brine. The organics were dried over Na$_2$SO$_4$ and concentrated under reduced pressure. Recrystallization twice from DCM:MeOH at −25° C. yielded the target compound as a green solid (0.593 g, 58% yield). $^1$H NMR (400 MHz, DMSO-d$_6$) δ 8.47 (d, J=7.6 Hz, 1H), 8.29 (d, J=8.4 Hz, 1H), 8.10 (d, J=8.4 Hz, 1H), 8.00 (d, J=7.6 Hz, 1H), 7.91 (ddd, J=8.3, 6.9, 1.2 Hz, 1H), 7.78 (ddd, J=8.3, 6.9, 1.2 Hz, 1H), 7.37 (d, J=2.3 Hz, 2H), 6.98 (dd, J=8.8, 2.4 Hz, 2H), 5.88 (d, J=8.8 Hz, 2H). $^{13}$C NMR (101 MHz, Benzene-d$_6$) δ 142.28, 140.84, 134.62, 133.14, 131.11, 130.13, 129.68, 129.44, 129.14, 128.69, 126.48, 123.98, 122.07, 117.10, 117.06, 115.84, 112.02.

Synthesis of 4-(3,7-Di([1,1'-Biphenyl]-4-yl)-10H-Phenothiazin-10-yl)-1-Naphthonitrile 4-(3,7-Dibromo-10H-phenothiazin-10-yl)-1-naphthonitrile (0.381 g, 0.750 mmol, 1.00 eq.) and 4-biphenylboronic acid (0.594 g, 3.00 mmol, 4.00 eq) were added to a 100 mL storage tube. After cycling the tube with N$_2$ and vacuum three times, the storage tube was taken into a nitrogen filled glove box. Pd(PPh$_3$)$_4$ (58.0 mg, 50.0 µmol, 5.00 mol %) was added to the storage tube and the mixture was dissolved in 20 mL THF. The storage tube was removed from the glove box and 10 mL of sparged 2 M K$_2$CO$_3$ was added. The resultant heterogeneous mixture was heated for 24 hours at 100° C. After the reaction was complete, the mixture was cooled to room temperature, exposed to oxygen, concentrated under reduced pressure and transferred to a separatory funnel, rinsing with DCM. The aqueous layer was extracted with DCM. The combined organics were washed with H$_2$O, brine, dried with Na$_2$SO$_4$ and concentrated under reduced pressure. The resultant solid was dissolved in toluene, passed through a silica plug and again concentrated under reduced pressure. Recrystallization from DCM:MeOH at −25° C. yielded the desired product as an orange solid (0.384 g, 78% yield). $^1$H NMR (400 MHz, DMSO-d$_6$) δ 8.53 (d, J=7.6 Hz, 1H), 8.34 (dt, J=8.4, 1.0 Hz, 1H), 8.23 (d, J=8.4 Hz, 1H), 8.08 (d, J=7.6 Hz, 1H), 7.94 (ddd, J=8.4, 7.0, 1.2 Hz, 1H), 7.82 (ddd, J=8.3, 6.9, 1.1 Hz, 1H), 7.75-7.64 (m, 12H), 7.54 (d, J=2.2 Hz, 2H), 7.47 (t, J=7.6 Hz, 4H), 7.41-7.32 (m, 2H), 7.20 (dd, J=8.6, 2.2 Hz, 2H), 6.06 (d, J=8.6 Hz, 2H). $^{13}$C NMR (101 MHz, Benzene-d$_6$) δ 142.69, 141.92, 141.17, 140.59, 138.72, 136.31, 134.76, 133.44, 131.78, 129.65, 129.17, 129.13, 129.08, 127.98, 127.65, 127.37, 127.08, 126.47, 125.93, 125.63, 124.63, 120.82, 117.33, 116.42, 111.84. HRMS (APCI): calculated for M+H C$_{47}$H$_{30}$N$_2$S, 655.2208; observed 655.2209.

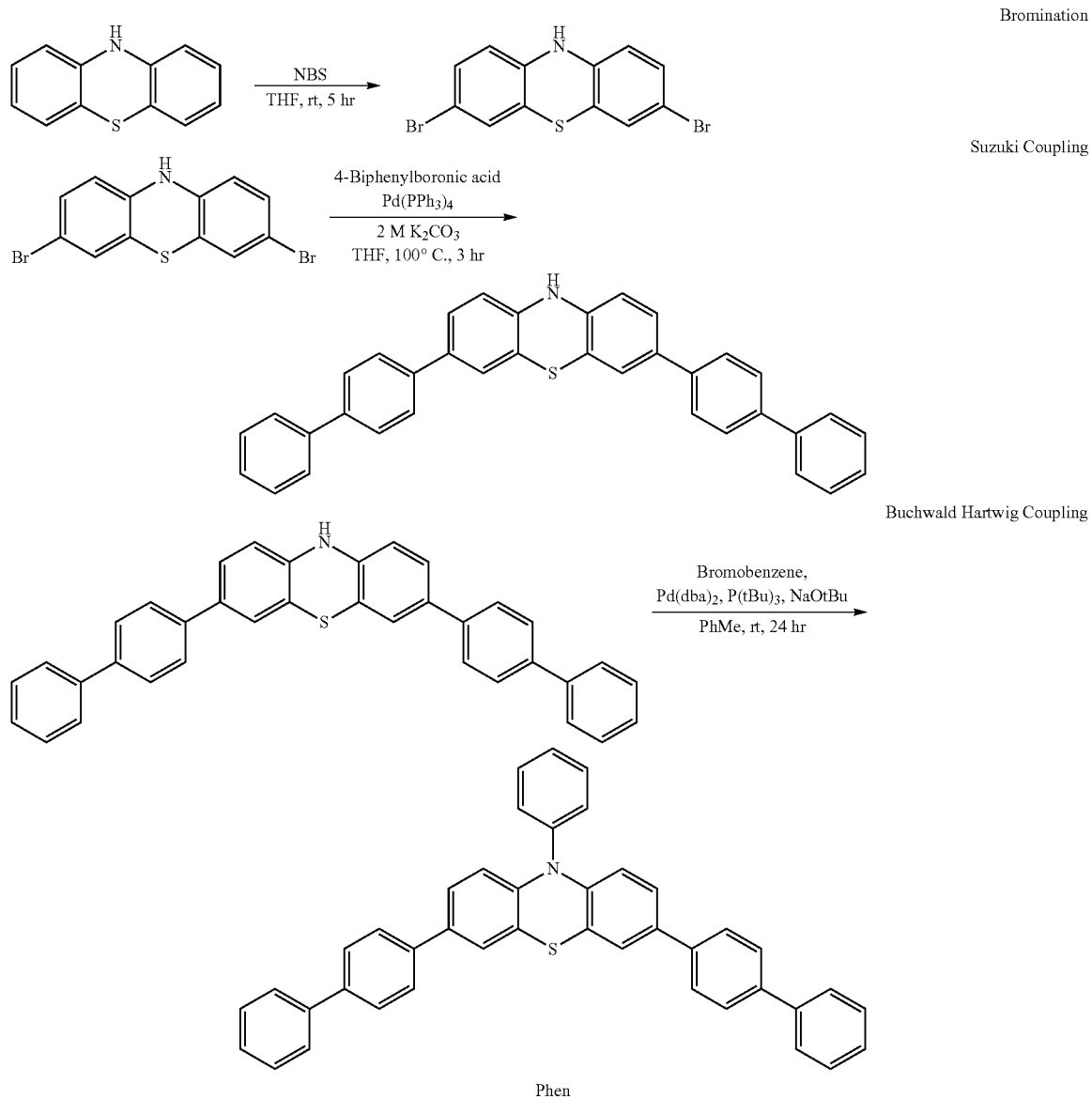

Scheme 1: Synthesis of Phen

Phen

3,7-Dibromo-10H-Phenothiazine

Phenothiazine (1.99 g, 10.0 mmol, 1.00 eq.) was added to a 200 mL schlenk flask equipped with an addition funnel and cycled with $N_2$ and vacuum 3×. THF (20 mL) was added and the flask was cooled to 0° C. NBS (3.93 g, 22.0 mmol, 2.20 eq.) was dissolved in 45 mL sparge and stabilized THF and added to the addition funnel. The entire apparatus was covered in foil and the NBS was added at ~1 drop/sec. After addition, the reaction was stirred for 4 hours. The crude reaction mixture was concentrated, re-dissolved in 1:1 EtOAc:hexanes and passed through a silica plug. The solvent was removed under reduced pressure and the solid was re-dissolved in toluene at ~50° C., cooled and the solid was collected by filtration, yielding the desired compound as a white powder (0.652 g, 18% yield). NMR matched previously reported.

3,7-Di([1,1'-Biphenyl]-4-yl)-10H-Phenothiazine 3,7-dibromo-10H-phenothiazine (0.250 g, 0.700 mmol, 1.00 eq.) and 4-biphenylboronic acid (0.554 g, 2.80 mmol, 4.00 eq) were added to a 100 mL storage tube. After cycling the tube with nitrogen and vacuum three times, the storage tube was taken into a nitrogen filled glove box. $Pd(PPh_3)_4$ (41.0 mg, 35.0 µmol, 5.00 mol %) was added to the storage tube and the mixture was dissolved in 14 mL THF. The storage tube was removed from the glove box and 7 mL of sparged 2 M $K_2CO_3$ was added. The resultant heterogeneous mixture was heated for 3 hours at 100° C. After the reaction was complete, the mixture was cooled to room temperature, exposed to oxygen, and filtered. The solid was washed with $H_2O$, MeOH, acetone and DCM yielding the desired product as a yellow solid (0.234 g, 66% yield). Due to very poor solubility, carbon NMR was unable to be obtained. $^1$H NMR (400 MHz, Chloroform-d) δ 7.69-7.61 (m, 9H), 7.57 (d, J=8.5 Hz, 4H), 7.46 (t, J=7.6 Hz, 4H), 7.40 (d, J=1.9 Hz, 2H), 7.39-7.34 (m, 2H), 7.23 (s, 2H), 7.19 (d, J=1.7 Hz, 2H). Not detected by mass spectrometry.

3,7-Di([1,1'-Biphenyl]-4-yl)-10-Phenyl-10H-Phenothiazine 3,7-di([1,1'-biphenyl]-4-yl)-10H-phenothiazine (0.151 g, 0.300 mmol, 1.00 eq.) and NaO$^t$Bu (43.3 mg, 0.450 mmol, 1.50 eq.) were added to a flame-dried 50 mL storage tube, cycled 3× through N$_2$ and vacuum, and brought into an N$_2$ filled glovebox. Pd(dba)$_2$ (8.6 mg, 15.0 µmol, 5.00 mol %), 1 M P($^t$Bu)$_3$ in toluene (12.0 µL, 12.0 µmol, 4.00 mol %) and 5 mL toluene were added and the storage tube was brought out of the glove box. Sparged bromobenzene (34.5 µL, 0.330 mmol, 1.10 eq) was added and the reaction mixture was heated at 50° C. for 24 hours. The reaction mixture was diluted with 50 mL toluene and passed through a silica plug. Solvent was removed under reduced pressure and the resulting solid was recrystallized from DCM:MeOH, yielding the desired product as a bright yellow solid (0.109 g, 63% yield). $^1$H NMR (400 MHz, DMSO-d$_6$) δ 7.78-7.66 (m, 14H), 7.63 (d, J=7.4 Hz, 1H), 7.53 (d, J=7.7 Hz, 2H), 7.51-7.43 (m, 6H), 7.37 (t, J=7.4 Hz, 2H), 7.32 (dd, J=8.4, 2.2 Hz, 2H), 6.19 (d, J=8.5 Hz, 2H). Due to very poor solubility, carbon NMR was unable to be obtained. HRMS (ESI): calculated for M+ C$_{42}$H$_{29}$NS, 579.2021; observed 579.2019.

Photophysical Characterization

Figure 12:
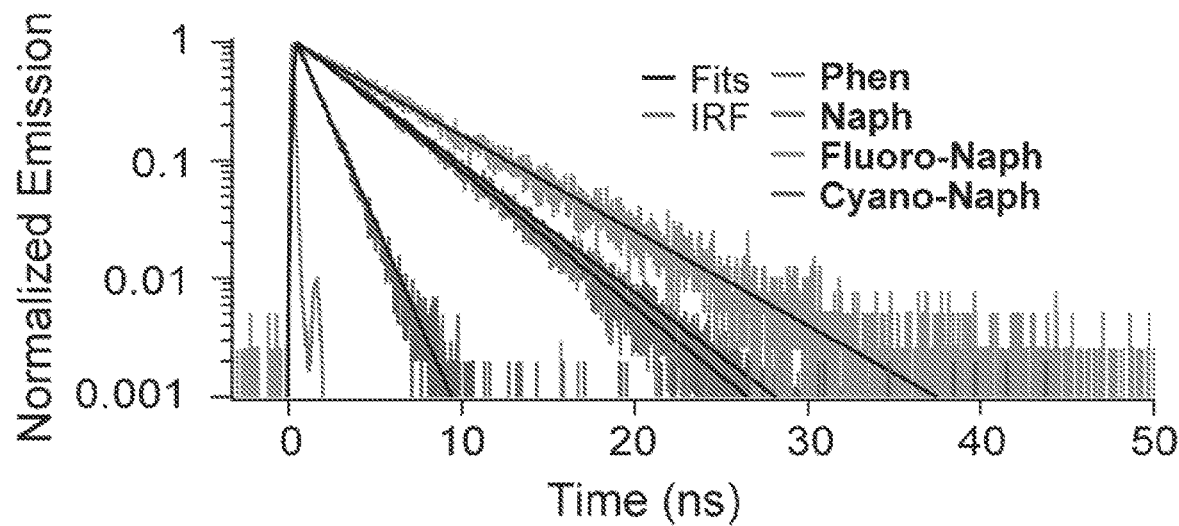
FIG. 12 shows TCSPC (Time Correlated Single Photon Counting) time traces of all four molecules in this study and their respective single-exponential fits convolved with Gaussian fit of IRF. These traces were collected at the wavelength of maximum fluorescence for all compounds but Fluoro-Naph. Fluoro-Naph data was collected at 650 nm due to an ultrafast component observed at lower wavelengths.
Figure 13:
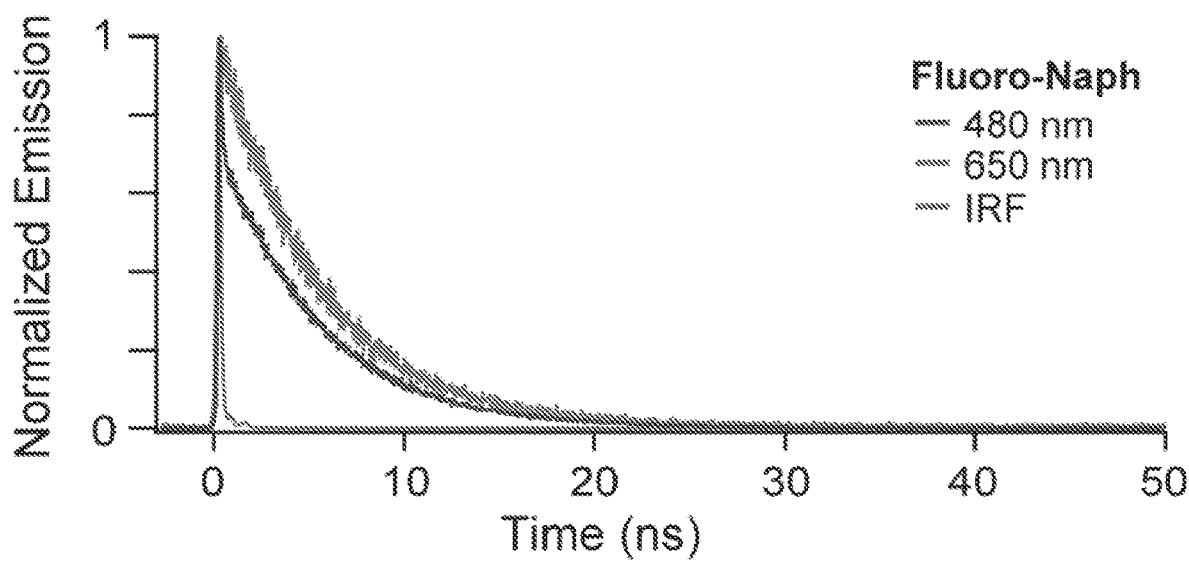
FIG. 13 shows TCSPC traces of Fluoro-Naph at 480 and 650 nm. The early emission component (IRF limited) at lower wavelengths indicates emission from a transiently occupied higher-lying excited state than the $S_1$.

For steady state experiments, Time Correlated Single Photon Counting (TCSPC) fluorescence lifetime experiments, Nanosecond Transient Absorption (NSTA) experiments, and triplet-triplet energy transfer (TTET) intersystem crossing yield ($\Phi_{ISC}$) experiments, samples were prepared in 1 cm×1 cm quartz cuvettes with optical densities near or below 0.1 at the excitation wavelength (FIG. 12 and FIG. 13).

All samples used anhydrous N,N-dimethylacetamide (DMAc) and were degassed prior to experiments by bubbling with argon for at least 15 minutes, except where otherwise stated. The anhydrous DMAc was purchased from Sigma Aldrich. Experiments with tetrahydrofuran (THF) and toluene used anhydrous solvent purchased from Sigma Aldrich.

All reported lifetimes and quantum yields with error bounds are the average of at least three independent measurements, and the reported error bounds are 2 times the standard deviation of a set of measurements.

Absorption and Emission Spectra and Emission Quantum Yield

Figure 9:
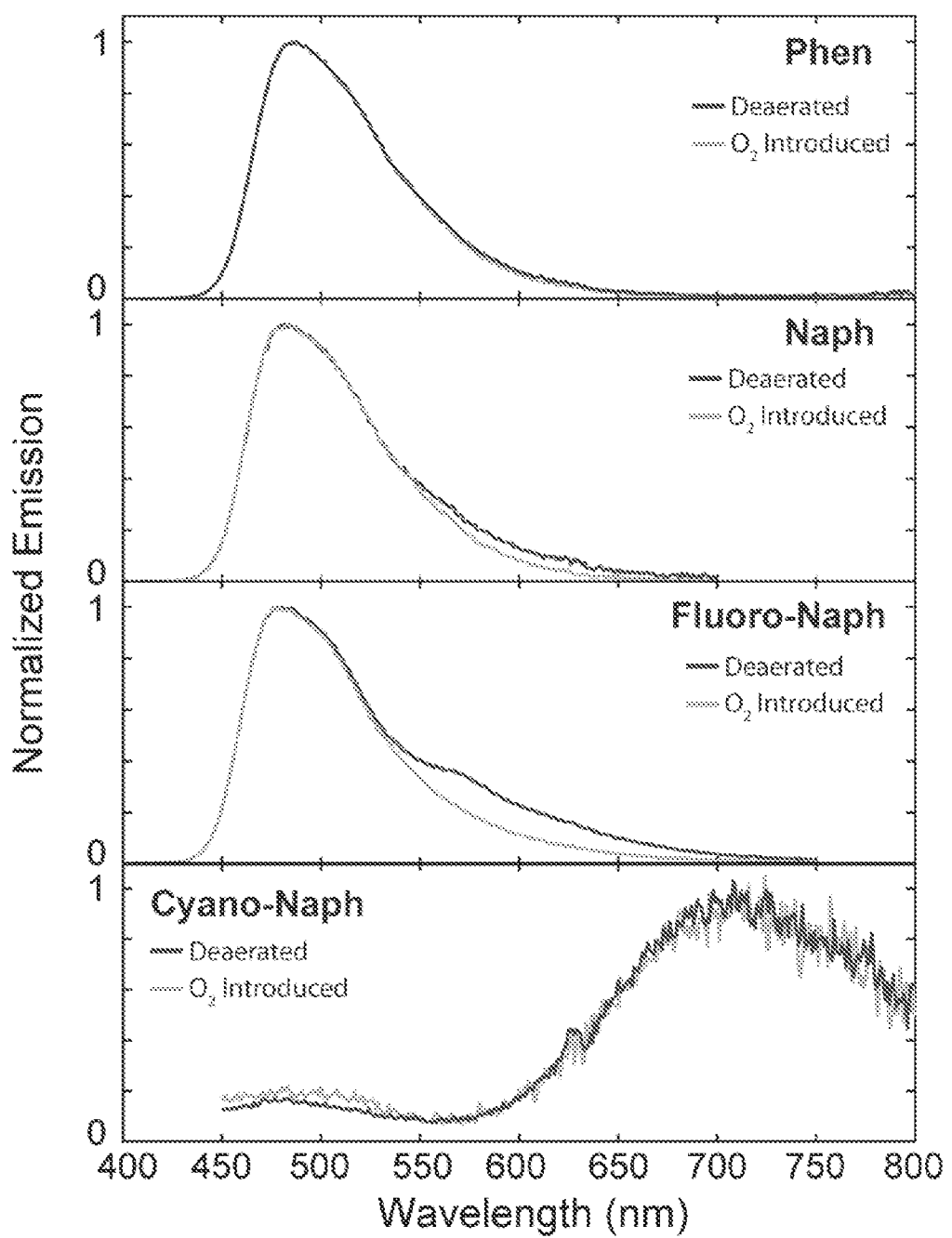
FIG. 9 shows normalized emission spectra of Phen, Naph, Fluoro-Naph, and Cyano-Naph taken in the absence of oxygen and, subsequently, in the presence of oxygen.

Absorption spectra were measured using an Agilent Cary 60 UV-Vis Spectrophotometer. Emission spectra (FIG. 9) were measured using an SLM 8000C Spectrofluorometer with the appropriate wavelength-dependent correction applied to the raw data. The quantum yield of emission ($\Phi_{em}$) was determined by the comparative method, using Coumarin 500 in methanol as the standard. In order to isolate the quantum yield of fluorescence ($\Phi_{fl}$) from $\Phi_{em}$, $\Phi_{em}$ was measured in the presence of oxygen (ambient air). In order to account for oxygen quenching of the singlet state, the singlet lifetime of the ambient air sample was measured. Then, $\Phi_{fl}$ of deaerated samples can be calculated in the following way: $\Phi_{fl}=(\Phi_{em,ambient\ air}*\tau_{singlet,ambient\ air}^{-1})/\tau_{singlet,deaerated}^{-1}$.

Molar Absorptivity

Molar absorptivities (ε) were determined by first preparing 5 solutions of known concentration for each compound in the range of 5-50 µM. This was done by dissolving a known mass (>5 mg) of compound to a known volume of DMAc (HPLC grade, Sigma Aldrich) and performing subsequent dilutions. Then, the absorbance spectra of these solutions were measured using an Agilent Cary 60 UV-Vis, and the absorbance at the wavelength of maximum absorbance ($\lambda_{max}$) was plotted as a function of concentration. For all compounds, these data fit to a linear function ($R^2 \geq 0.9998$), indicating linear Beer-Lambert behavior. Thus, the slopes of these fits were taken as the $\varepsilon(\lambda_{max})$ for each compound.

Cyclic Voltammetry (CV)

Figure 17:
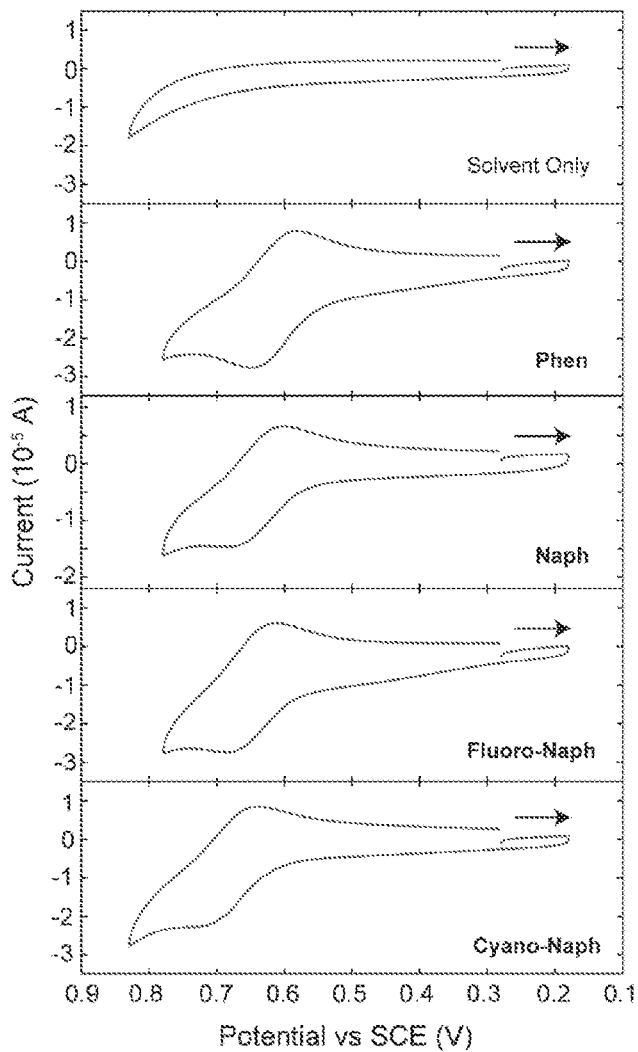
FIG. 17 shows cyclic voltammograms of Phen, Naph, Fluoro-Naph, and Cyano-Naph, taken at a scan rate of 50 mV/s. Arrows indicate the initial scan direction.

CV measurements were performed using a 3-electrode technique, which employed a 0.01 M Ag/AgNO$_3$ reference electrode and a CH Instruments 601C electrochemical analyzer (FIG. 17). For both the reference and sample electrodes (platinum working and counter electrodes were used), anhydrous DMAc was used for the solvent and 0.1 M tetrabutylammonium hexafluorophosphate (purchased from Sigma Aldrich) was used as the electrolyte. Potentials versus the standard calomel electrode (SCE) were determined by employing the oxidation of ferrocene as an internal standard and then adding 380 mV.

Spectroelectrochemical Measurements

Figure 18:
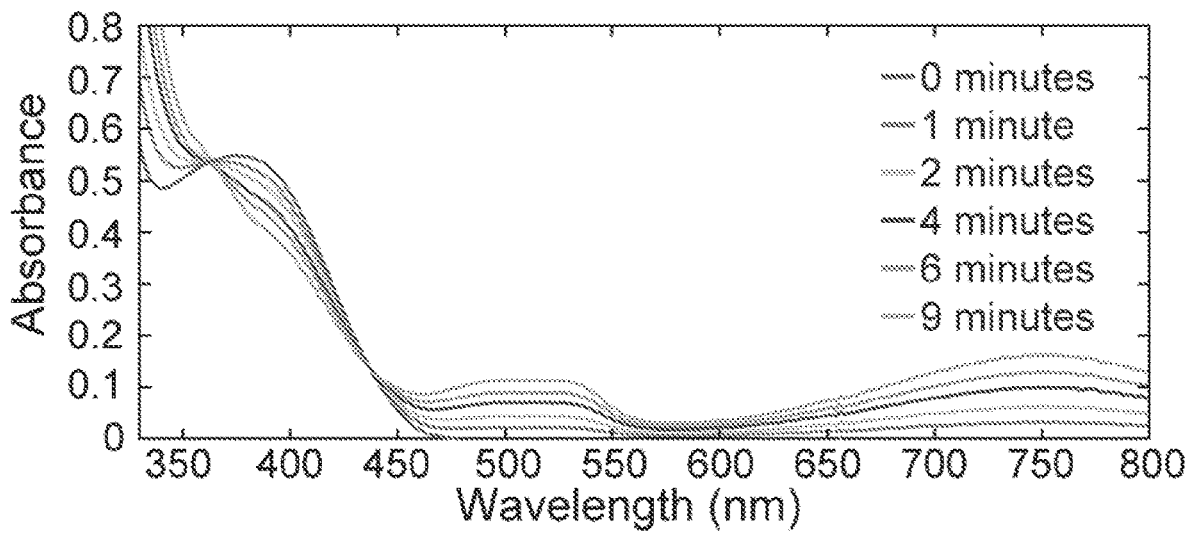
FIG. 18 shows spectroelectrochemical data of Naph at various time delays following the onset of bulk electrolysis at a potential of 0.75 V vs SCE, in RT DMAc.

Spectroelectrochemistry experiments were conducted using a home-built glass optically transparent thin layer electrode cell with a 0.2 cm path length and a Pt mesh working electrode, a Pt wire counter electrode, and a freshly prepared 0.01 M Ag/AgNO$_3$ reference electrode which used anhydrous DMAc for the solvent (FIG. 18). 0.1 M tetrabutylammonium hexafluorophosphate (TBAPF$_6$) was used as the electrolyte. The sample was dissolved in anhydrous DMAc, degassed with Ar, then blanketed with Ar for the duration of the experiment. Bulk electrolysis of the sample was performed using an electrochemical analyzer (CH Instruments 601C), and electronic absorption spectra were acquired using a Hewlett Packard diode array UV-vis spectrophotometer (HP8452A).

Time-Correlated Single Photon Counting (TCSPC) and Time-resolved Emission

Time-resolved emission measurements were made using a DeltaFlex Modular Fluorescence Lifetime System from Horiba Scientific. For TCSPC measurements, a Horiba NanoLED-405L was used as the excitation source (402 nm, <200 ps pulse duration) and emission was detected at magic angle. TCSPC traces were fit to a model of exponentials convoluted with a Gaussian fit of the instrument response function (FWHM of ~230 ps), with the lowest number of exponentials used that would give a reasonable fit. This always resulted in a fit which required only a single exponential, although an offset was often required to account for phosphorescence when fitting singlet lifetimes.

For longer timescale time-resolved emission measurements (>µs), a Horiba SpectraLED (417±18 nm) was used as the excitation source. Here, emission traces were fit to a simple single-exponential model.

Nanosecond Transient Absorption (NSTA)

NSTA spectra were acquired using a Edinburgh Instruments LP980KS spectrometer equipped with a Continuum Minilite Nd:YAG Q-switched laser (355 nm) and an Andor iStar ICCD camera.

NSTA lifetime and TTET measurements were made using a previously described home-built setup. $\Phi_{ISC}$ was measured using a TETT method described previously, with fac-Ir(ppy)$_3$ (purchased from Sigma Aldrich) as the sensitizer.

Femtosecond Transient Absorption (FSTA)

FSTA data were collected using a previously described home-built setup. Samples were prepared and sealed in a quartz cuvette with a path length of 0.2 cm. Samples were excited at 400 nm and were prepared such that the percent of molecules excited per pulse was kept near or under 5%. FSTA data were fit to an exponential model using an in-house global fitting procedure.

Oxygen Sensitivity of Steady-State Emission

In order to assess the $O_2$ sensitivity of the steady-state of Phen, Naph, Fluoro-Naph, and Cyano-Naph in DMAc, emission spectra of each species were measured after purging with argon for at least 20 minutes, and, following this, the emission of each sample was measured after being exposed to ambient air. The results, shown in the following figure, demonstrate that Naph, and Fluoro-Naph (and to some extent, Phen) possess different emission profiles under these different conditions, indicating the presence of at least two emitting states with different timescales for emission (i.e., fluorescence and phosphorescence).

Fitting the Fluorescence Spectra of Phen and Naph

Figure 11:
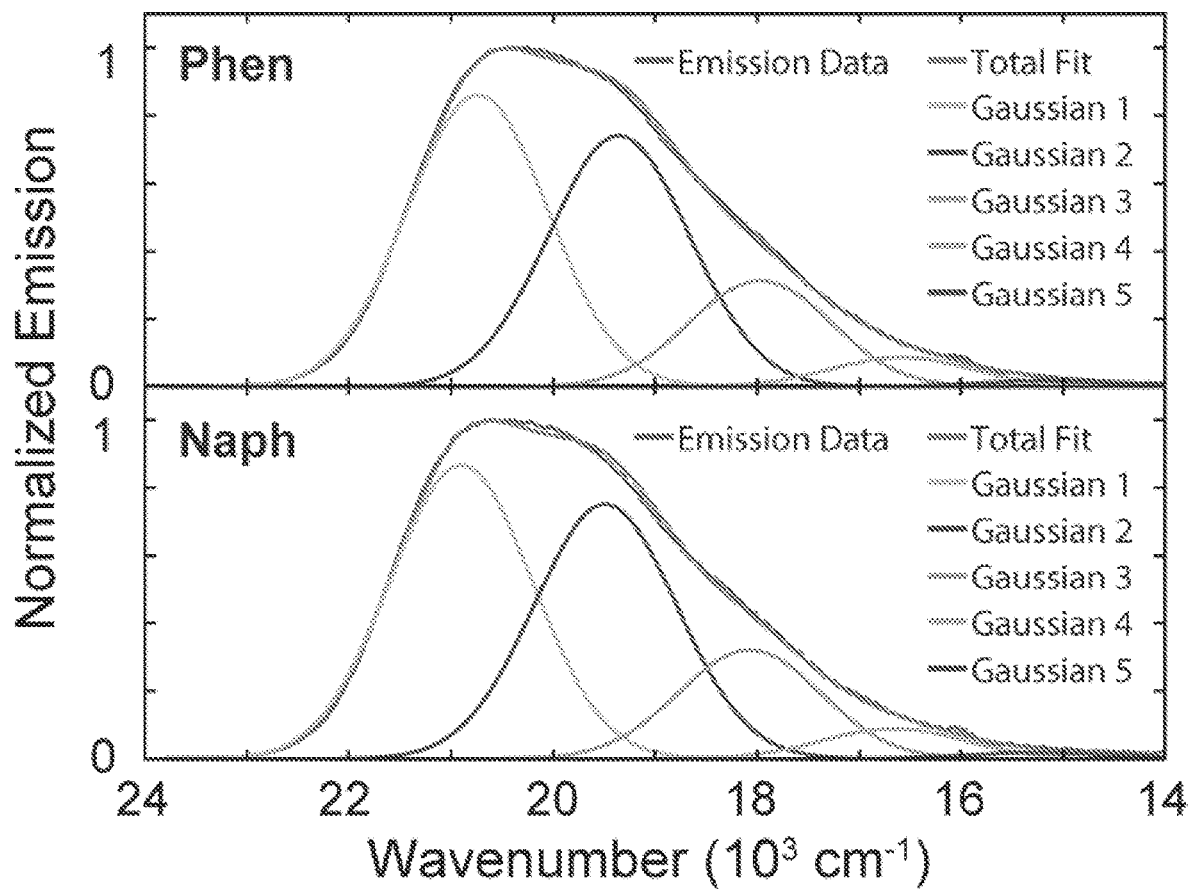
FIG. 11 shows fluorescence spectra and fits of Phen and Naph in DMAc at 20° C.

To determine the energy of $S_{deloc}$, the fluorescence spectra of Phen and Naph were each fit to a vibronic progression to extract $E_0$, which is then converted to $E_{00}$ by consideration of the spectral linewidth (FIG. 11). The number of Gaussians used for the fit was determined as the number after which an additional Gaussian would not improve the fit. The fluorescence spectra of Fluoro-Naph and Cyano-Naph could not be fit to vibronic progressions. For Fluoro-Naph, this is presumably due to the presence of two distinct emitting state resulting from the more significant contribution of $S_{CT-Naph}$ emission. For Cyano-Naph, this is due to the fact that emission from $S_{CT-Naph}$ is so broad that vibronic peaks cannot be distinguished.

TABLE 2

Fit parameters to the fluorescence spectra of Phen and Naph in DMAc at 20° C.

| | Phen | Naph |
| --- | --- | --- |
| $E_{00}$ (eV) | 2.713 | 2.736 |
| $E_0$ (eV) | 2.571 | 2.591 |
| ω (cm$^{-1}$) | 1385 | 1413 |
| FWHM (cm$^{-1}$) | 1622 | 1637 |
| S | 1.059 | 1.070 |

Assignment of $S_{deloc}$

The assignment of the fluorescent state of Phen and Naph is aided by the context of the phenoxazine analogues to Phen, which have been previously characterized. The chemical analogues discussed in this section are shown below.

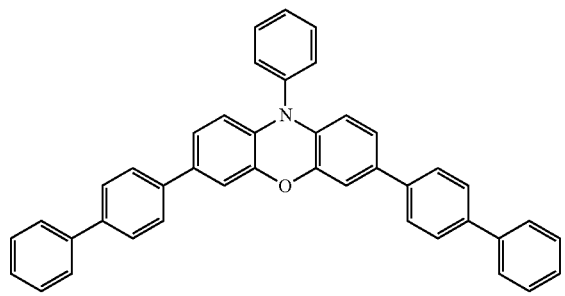

1

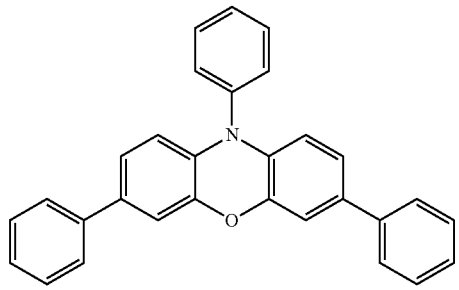

1'

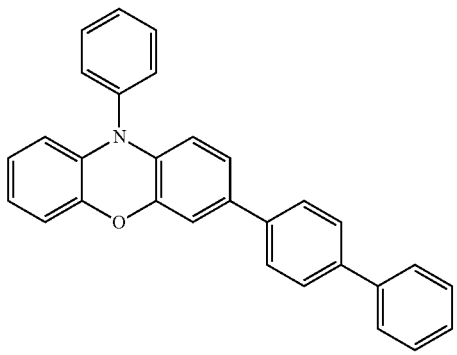

1a

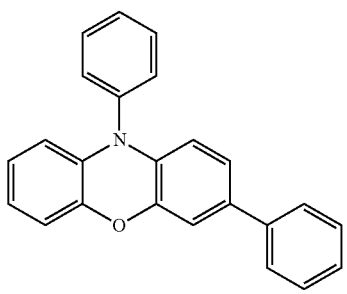

1a'

The direct phenoxazine analogue to Phen (1) possesses distinct fluorescence behavior from Phen and Naph. 1 has a higher degree of solvatochromism and a broader fluorescence profile—both of which indicate a more polar $S_1$. The assignment of the $S_1$ of 1 was additionally aided by comparison its fluorescence behavior to that of a chemical analogue, 1a, which possesses only a single biphenyl substituent. Along with the broad, solvatochromic fluorescence of 1, the similarity of the fluorescence behavior of 1 and 1a led to the assignment of the $S_1$ of 1 as $S_{CT-Biph}$, in which charge is transferred from the phenoxazine moiety to a single biphenyl substituent.

In contrast to 1, a separate phenoxazine compound analogue to Phen (called 1') exhibits similar emission behavior to that of Phen and Naph. 1' possesses a more structured fluorescence profile than 1 and is only weakly solvatochromic. As with 1, the fluorescence of 1' was characterized by comparison to a chemical analogue, 1a', in which one of the phenyl substituents is absent. The fluorescence behavior of 1a' was found to be distinct from 1', being broader and more highly solvatochromic. This difference between 1' and 1a' indicates that while the $S_1$ of 1a' is a CT state (from the phenoxazine to a single phenyl substituent), possesses a less polar $S_1$ state which involves both phenyl substituents. Consequently, the $S_1$ of 1' has been assigned as $S_{deloc}$. The similarity of the fluorescence behavior of Phen and Naph to 1', and the contrast of Phen and Naph's fluorescence behavior with 1, leads to the assignment of the $S_1$ of Phen and Naph as $S_{deloc}$.

TCSPC Kinetic Traces and Phosphorescence Lifetimes

Time-resolved emission traces of the phosphorescence of Phen, Naph, and Fluoro-Naph in RT anhydrous DMAc were measured. However, the lifetimes of each compound were not found to be reproducible between measurements of independently prepared samples. This may be to be due to variable concentrations of oxygen, to which the triplet lifetimes of the compounds are extremely sensitive, owing to their long lifetimes. While preparation of samples in a glovebox utilizing ultra-high-purity nitrogen resulted in relatively consistent lifetime measurements among the compounds (~15 ms), sample preparation which employed purging with argon resulted in longer lifetimes than 15 ms in multiple instances. However, these lifetimes were not readily reproducible. Therefore, the triplet lifetimes of Phen, Naph, and Fluoro-Naph are uncertain and are reported as greater than 15 ms.

Phosphorescence Spectra and Spectral Fitting

Figure 14:
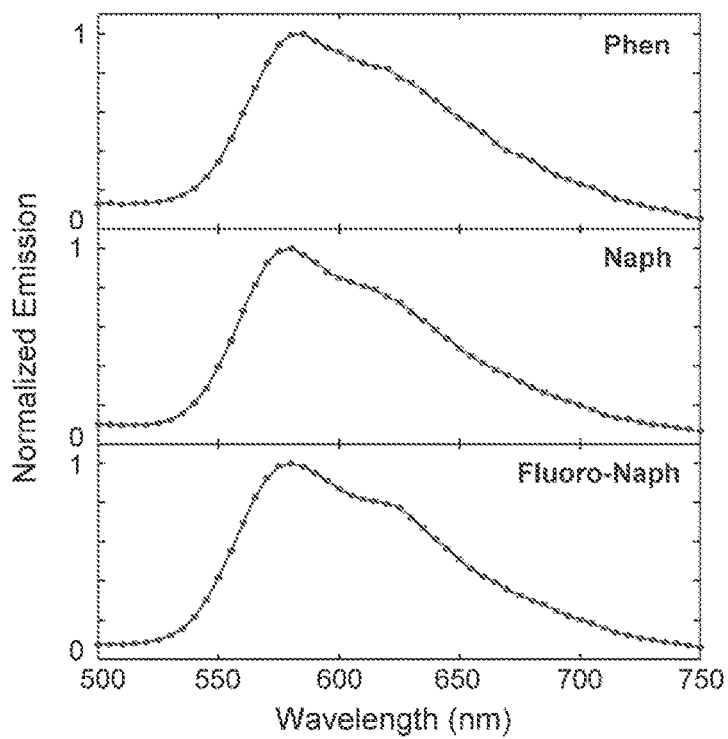
FIG. 14 shows phosphorescence spectra of Phen, Naph and Fluoro-Naph in RT DMAc.
Figure 15:
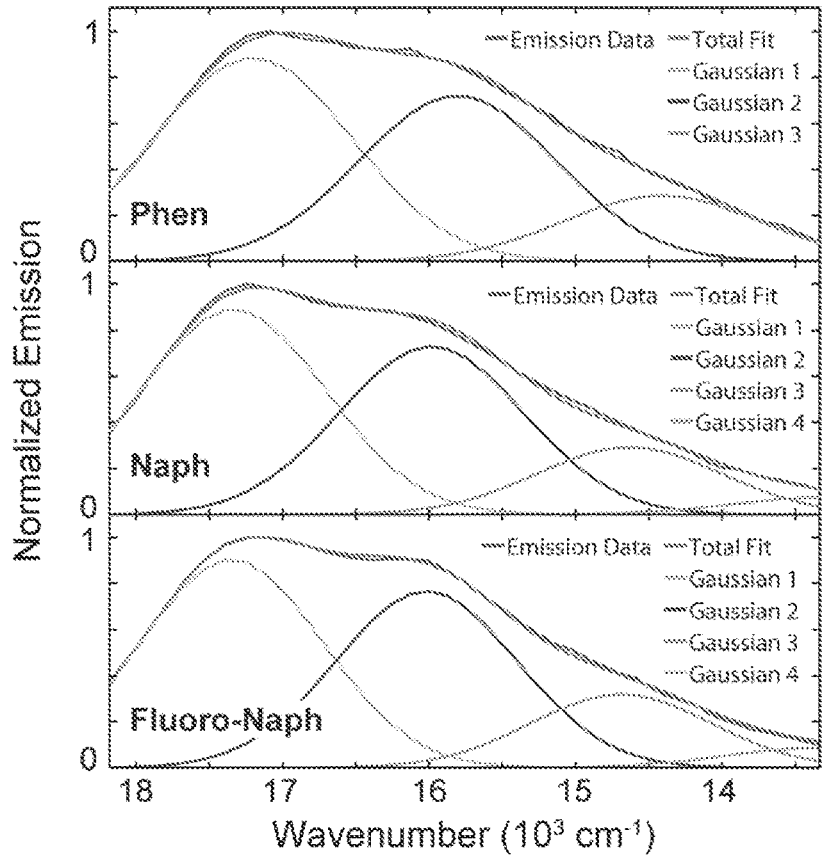
FIG. 15 shows phosphorescence spectra and fits of Phen, Naph and Fluoro-Naph in RT DMAc.

The phosphorescence spectra of Phen, Naph, and Fluoro-Naph were measured by collecting time-resolved emission traces at multiple wavelengths for a fixed time duration at each wavelength (FIG. 14 and FIG. 15). The individual traces were integrated starting at a sufficient delay (on the order of milliseconds) in order to generate phosphorescence spectra. We note that a slight amount of fluorescence remains, due to triplet-triplet annihilation (TTA), which results in emission features which extend to ~525 nm. These spectra were then corrected to account for variable PMT response at different wavelengths. The corrected phosphorescence spectra were trimmed slightly to exclude fluorescence resulting from TTA and then fit to a vibronic progression in a manner similar to the fitting of fluorescence spectra described earlier.

TABLE 3

Fit parameters to the phosphorescence spectra of Phen, Naph, and Fluoro-Naph in RT DMAc.

|  | Phen | Naph | Fluoro-Naph |
| --- | --- | --- | --- |
| $E_{00}$ (eV) | 2.267 | 2.268 | 2.264 |
| $E_0$ (eV) | 2.133 | 2.149 | 2.151 |
| ω (cm$^{-1}$) | 1394 | 1351 | 1329 |
| FWHM (cm$^{-1}$) | 1580 | 1482 | 1453 |
| S | 1.048 | 1.044 | 1.079 |

TABLE 4

Electrochemical data for compounds (C), values in Volts vs SCE.

|  | $E_{1/2}$ (C$^{\bullet+}$/C) | $\Delta E_p$ (C$^{\bullet+}$/C) |
| --- | --- | --- |
| Phen | 0.61 | 0.073 |
| Naph | 0.64 | 0.074 |
| Fluoro-Naph | 0.65 | 0.076 |
| Cyano-Naph | 0.68 | 0.085 |

Simulation of Late-Time FSTA Spectrum of Naph

Figure 19:
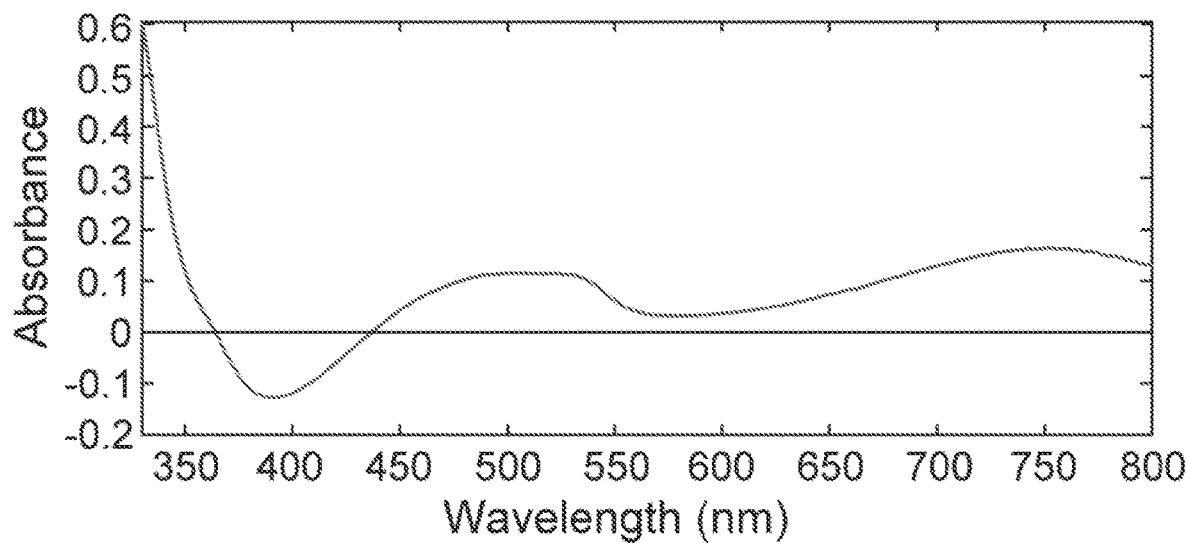
FIG. 19 shows the oxidative difference spectrum of Naph, generated by subtracting the ground state spectrum from the spectrum acquired at the latest time delay (9 minutes).
Figure 20:
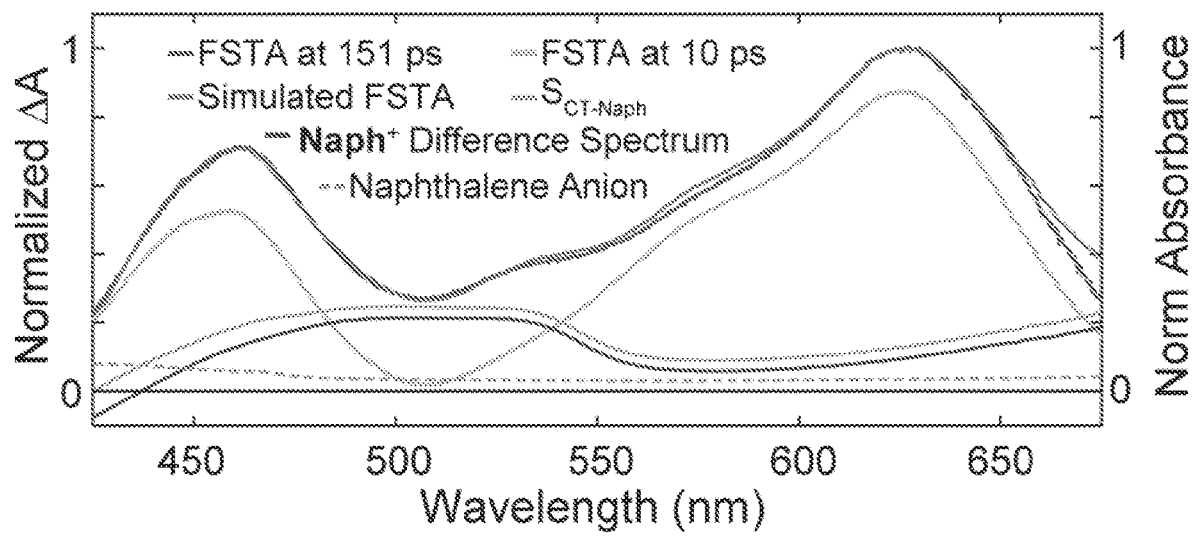
FIG. 20 shows the observed and simulated late-time FSTA spectra of Naph, with the redox-derived data and early-time FSTA spectrum used for simulation. $S_{CT-Naph}$ consists of 'Naph$^+$ Difference spectrum'+'Naphthalene Anion'. Solid and dashed lines refer to $\Delta A$ and absorbance spectra, respectively.

The late-time FSTA spectrum of Naph was simulated using the following: an early-time FSTA spectrum of Naph (10 ps), the oxidative difference spectrum of Naph, and the absorption spectrum of a naphthyl radical anion (FIG. 19 and FIG. 20). The former spectrum is used to account for the remaining $S_{deloc}$ at late times, and the latter two spectra are used to simulate $S_{CT-Naph}$. The 10 ps spectrum, in particular, is chosen to reflect the relaxed $S_{deloc}$ but is sufficiently early such that no significant $S_{CT-Naph}$ formation has taken place (FIG. 16). The ability to model the late-time spectrum with these three basis spectra is strong evidence that the $S_1$ of Naph consists of an equilibrium between $S_{deloc}$ and $S_{CT-Naph}$. Furthermore, this modelling can be used to estimate the relative concentrations of each species in equilibrium and therefore the equilibrium constant. This is done in the following way:

Since the 10 ps spectrum follows the cooling of $S_{deloc}$ but precedes significant $S_{CT-Naph}$ formation, ΔA at 10 ps may be taken as corresponding to the initial concentration of $S_{deloc}$. Between 10 ps and 151 ps, the ΔA at the $\lambda_{max}$ of $S_{deloc}$ (625 nm) falls from 11.1 mOD to 7.4 mOD. If no other features grew in during this time, this would indicate a ~67% decrease in $S_{deloc}$ concentration. However, $S_{CT-Naph}$ is formed during this time, and this new state possesses ΔA features at 625 nm. To quantify how significant this contribution from $S_{CT-Naph}$ is, we can monitor the growth of $S_{CT-Naph}$ features in a region in which $S_{deloc}$ has a very low ΔA (e.g., 505 nm). Between 10 ps and 151 ps, the ΔA at 505 nm grows by 1.76 mOD. Due to the goodness fit of the modeled FSTA with the 151 ps spectrum, the spectrum of $S_{CT-Naph}$ is considered to be well defined. Using the spectrum of $S_{CT-Naph}$, it is determined that a 1.76 mOD increase at 505 nm corresponds to a 0.91 mOD increase at 625 nm. With this taken into account, we see that the ΔA signal, which consists of a contribution from $S_{deloc}$ drops, from 11.1 mOD to 6.5 mOD between 10 ps to 151 ps. This corresponds to a drop in $S_{deloc}$ concentration to ~59% of the initial concentration. As there is no significant ground-state recovery on this timescale, it therefore is inferred that $S_{CT-Naph}$ constitutes 41% of the excited state population. This corresponds to an equilibrium constant of 0.695, which in turn, at RT (22.2° C., in this instance) corresponds to an energy difference of ~9 meV.

Comparing $k_{ISC}$ of Phenothiazine and Phenoxazine Analogues

The direct phenoxazine analogue to Phen (1) has a $k_{ISC}$ value of 3.8×10$^7$ s$^{-1}$, which is less than half that of Phen despite its greater driving force for ISC (~0.7 eV) for 1 versus 0.45 eV for Phen). However, ISC for the phenoxazine analogue to Phen represents a different electronic transition than for Phen, as the two compounds have $S_1$ states of different electronic character. A more suitable comparison for Phen may be the phenoxazine analogue to Phen in which the biphenyl substituents have been replaced with phenyl substituents (1'). For this second analogue, as with Phen, ISC consists of a transition from $S_{deloc}$ to a $T_1$ which consists of a core-localized (i.e., involving the 3- or 7-substituent) CT state. This second analogue has a $k_{ISC}$ value of 9.3×10$^7$, which is comparable to Phen. However, the driving force for ISC is higher for the phenoxazine analogue (0.74 eV) relative to Phen (0.45 eV). These results indicate that there may be higher spin-orbit coupling for Phen, arising from the heavy atom effect, but that competing effects which lower the driving force for ISC cancel out this spin-orbit coupling advantage.

The direct phenoxazine analogue to Naph has a $k_{ISC}$ value of 1.8×10$^8$ s$^{-1}$. ISC for this analogue consists of a comparable electronic transition to that of Fluoro-Naph (i.e., $SC_{T-Naph} \rightarrow T_{CT-Biph}$), and both compounds possess highly similar $k_{ISC}$ values. However, the driving force for ISC is higher for the phenoxazine analogue (~0.6 eV) than for Fluoro-Naph (0.47 eV). Similar to Phen, these results suggest the possibility of a higher spin-orbit coupling for Fluoro-Naph but that a lower driving force for ISC cancels out this advantage.

Computed Nuclear Geometries

All calculations utilized the GAUSSIAN 16 Revision A.03 computational chemistry package. Lowest energy singlet state and triplet state geometries, as well as triplet energies ($E_{T1}$), of all compounds were computed at the uM06/6-31+g(d,p)/CPCM-n,n-dimethylacetamide level of theory (Table 5). $E_{T1}$ was calculated as the difference in energy (not zero-point energy or thermally corrected) between the lowest energy singlet and lowest energy triplet states.

TABLE 5

Computed Triplet Energies

| | $E_{T1}$ (eV) |
|---|---|
| Phen | 2.34 |
| Naph | 2.34 |
| Fluoro-Naph | 2.40 |
| Cyano-Naph | 2.03 |

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein $\Phi_{ISC}$ losed may be resorted to by those of ordinary skill in the art, and that such modifications and variations are considered to be within the scope of embodiments of the present application.

Enumerated Embodiments

The following enumerated embodiments are provided, the numbering of which is not to be construed as designating levels of importance:

Embodiment 1 provides a compound of Formula I:

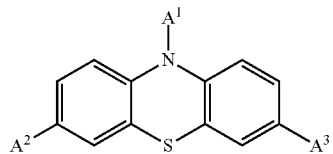

Formula I wherein:
each of $A^1$, $A^2$, and $A^3$ is independently an optionally substituted $C_{6-18}$ aryl, wherein the optional substitution is from 1 to 12 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)_2$, $OC(O)N(R)_2$, and $C(S)N(R)_2$;
wherein R is independently at each occurrence hydrogen or $C_{1-10}$ hydrocarbyl, provided that the compound of Formula I is not:

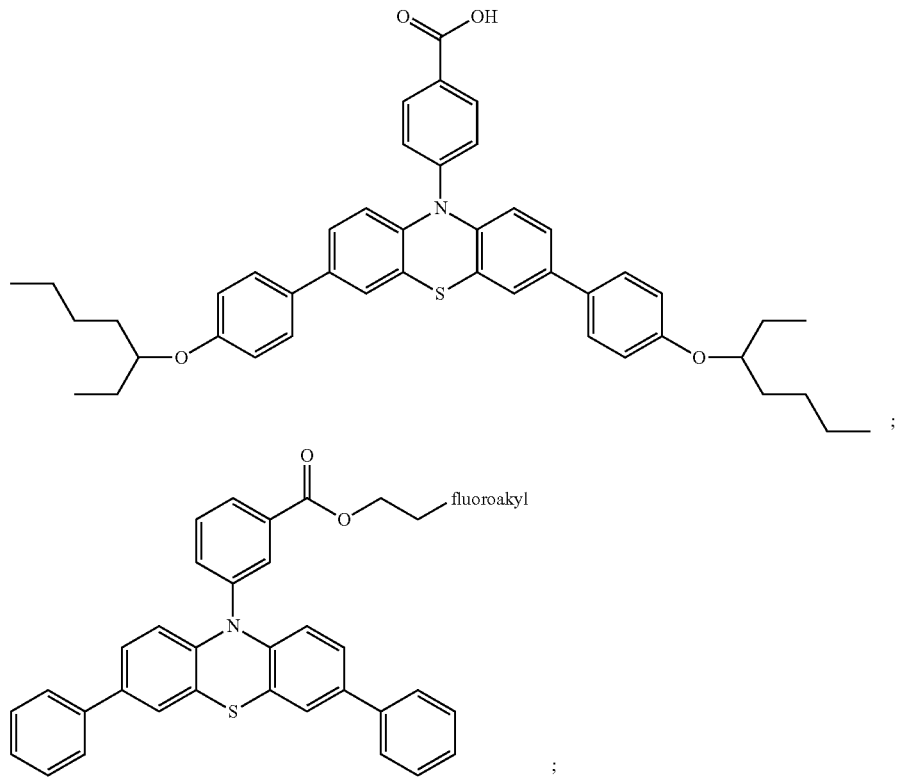

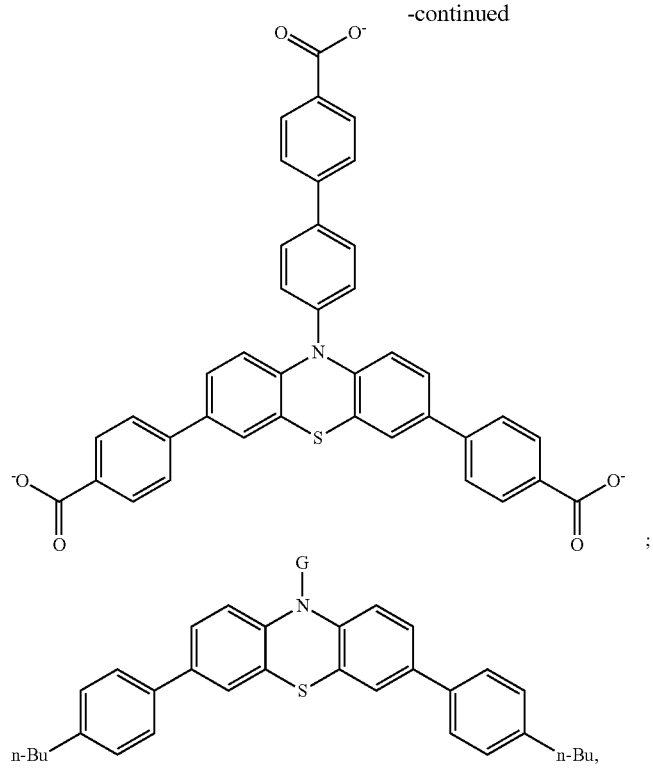

;

or salts thereof, wherein G is

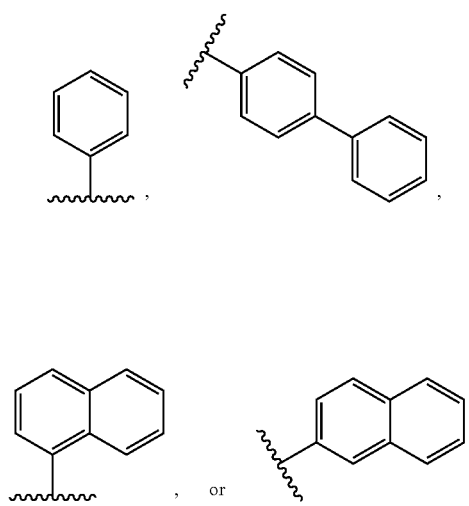

Embodiment 2 provides the compound of embodiment 1, wherein $A^1$, $A^2$ and $A^3$ are independently selected from the group consisting of:

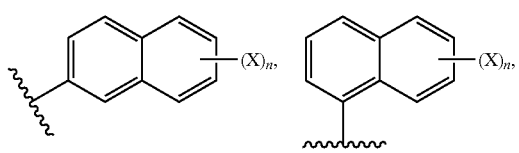

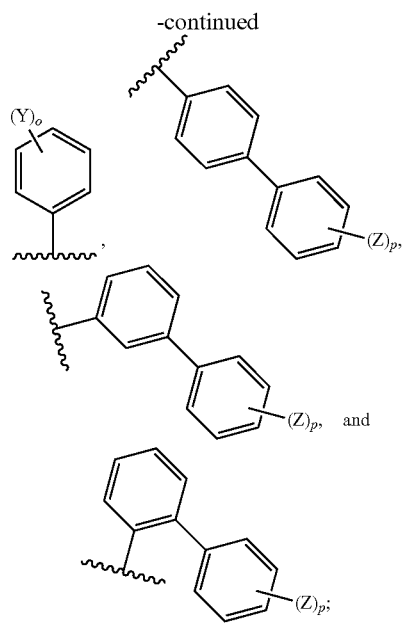

wherein each occurrence of X, Y, and Z is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)$_2$, OC(O)N(R)$_2$, and C(S)N(R)$_2$, n is an integer from 0 to 7;
o is an integer from 0 to 5; and
p is an integer from 0 to 9.

Embodiment 3 provides the compound of any one of embodiments 1-2, wherein $A^1$, $A^2$, and $A^3$ are independently selected from the group consisting of:

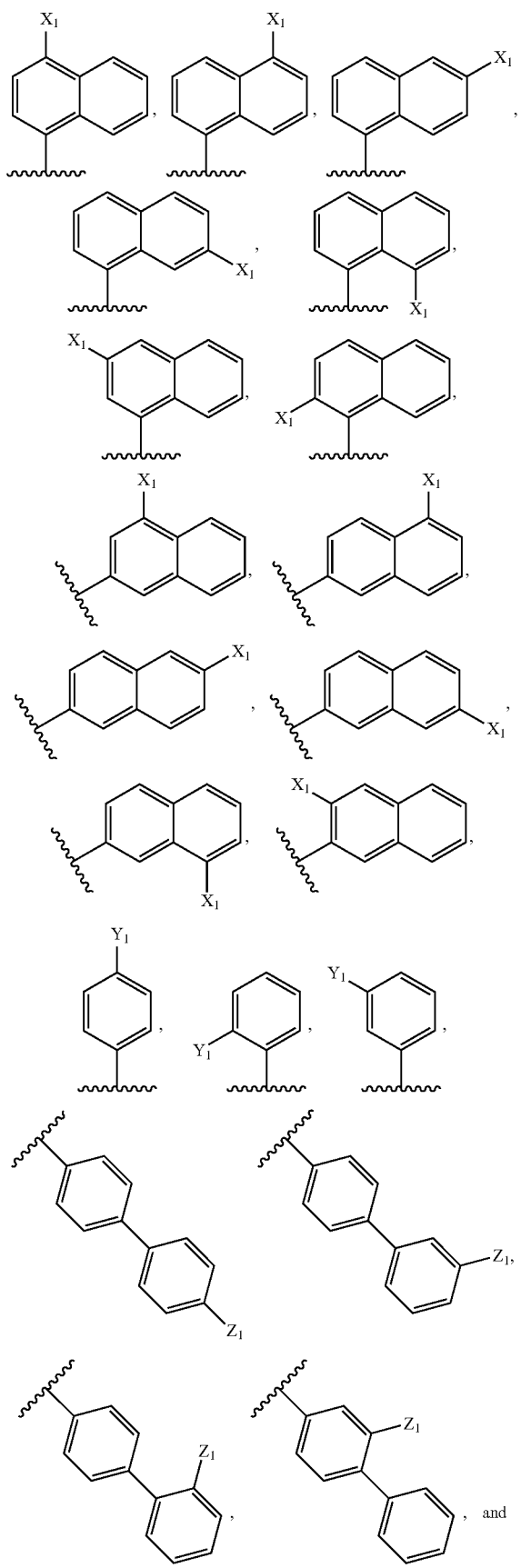

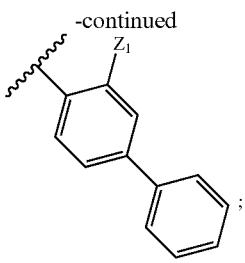

wherein each occurrence of $X_1$, $Y_1$, and $Z_1$ is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)_2$, $OC(O)N(R)_2$, and $C(S)N(R)_2$.

Embodiment 4 provides the compound of any one of embodiments 1-3, wherein $A^2$ and $A^3$ are $C_{6-12}$ aryl.

Embodiment 5 provides the compound of any one of embodiments 1-4, wherein $A^2$ and $A^3$ are biaryl.

Embodiment 6 provides the compound of any one of embodiments 1-5, wherein $A^2$ and $A^3$ are 4,4'-biphenyl.

Embodiment 7 provides the compound of any one of embodiments 1-6, wherein $A^1$ is a $C_{10}$ aryl substituted by 1 to 7 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$.

Embodiment 8 provides the compound of any one of embodiments 1-7, wherein $A^1$ is 1-naphthyl or 2-naphthyl.

Embodiment 9 provides the compound of any one of embodiments 1-8, wherein $A^1$ is

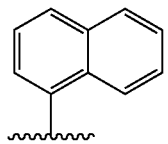

Embodiment 10 provides the compound of any one of embodiments 1-9, wherein $A^1$ is 1-naphthyl or 2-naphthyl is mono-substituted by a group selected from the group consisting of F, Cl, Br, CN, and $NO_2$.

Embodiment 11 provides the compound of any one of embodiments 1-10, wherein $A^1$ is substituted by F or CN.

Embodiment 12 provides the compound of any one of embodiments 1-11, wherein $A^1$ is

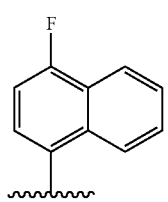

Embodiment 13 provides the compound of any one of embodiments 1-12, wherein $A^1$ is

[Structure: naphthalene with CN at position 1 and wavy bond at position 4]

Embodiment 14 provides a photocatalyst comprising the compound of any one of embodiments 1-13.

Embodiment 15 provides a method of polymerizing a substrate, the method comprising:
  providing a composition comprising at least one monomer and at least one compound of claim 1; and
  irradiating the composition with electromagnetic radiation,
  wherein the composition is free from metals.

Embodiment 16 provides the method of embodiment 15, wherein the at least one monomer comprises at least one of acrylates, styrene, acrylamides, acrylonitrile, vinyl chloride, methylacrylonitrile, vinyl acetate, acrylic acid, or mixtures thereof.

Embodiment 17 provides the method of any one of embodiments 15-16, wherein the composition further comprises at least one radical initiator.

Embodiment 18 provides the method of any one of embodiments 15-17, wherein the electromagnetic radiation is UV or visible light.

Embodiment 19 provides the method of any one of embodiments 15-18, wherein the compound of Formula I is present in an amount of about 0.01 to about 40% (w/w).

Embodiment 20 provides the method of any one of embodiments 15-19, wherein the at least one monomer is present in an amount of about 0.1 to about 99% (w/w).

Embodiment 21 provides a method of photocatalytically cross-coupling a substrate, the method comprising:
  providing a composition comprising:
    at least one substrate capable of undergoing a photochemical transformation
    at least one second substrate;
    at least one compound of any one of embodiments 1-14;
  cross-coupling the at least one substrate with the at least one second substrate and irradiating the composition with electromagnetic radiation.

Embodiment 22 provides a method of photocatalytically reacting a substrate via atom transfer radical addition (ATRA), the method comprising:
  providing a composition comprising:
    at least one substrate capable of undergoing an atom transfer radical addition (ATRA) reaction;
    at least one second substrate;
    at least one compound of any one of embodiments 1-14;
  reacting the at least one substrate with the at least one second substrate and irradiating the composition with electromagnetic radiation.

Embodiment 23 provides a method of photocatalytically reacting a substrate via free radical addition or free radical substitution, the method comprising:
  providing a composition comprising:
    at least one substrate capable of undergoing free radical reaction;
    at least one second substrate;
    at least one compound of any one of embodiments 1-14;
  reacting the at least one substrate with the at least one second substrate and irradiating the composition with electromagnetic radiation.

What is claimed is:

1. A compound of Formula I:

Formula I

[Phenothiazine structure with $A^1$ on N, $A^2$ and $A^3$ on the phenyl rings]

wherein:

each of $A^1$, $A^2$, and $A^3$ is independently an optionally substituted $C_{6-18}$ aryl, wherein the optional substitution is from 1 to 12 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, and $C(S)N(R)_2$;

wherein R is independently at each occurrence hydrogen or $C_{1-10}$ hydrocarbyl, provided that the compound of Formula I is not:

[Structure of phenothiazine derivative with benzoic acid on N and two alkoxyphenyl groups]

;

[Structure of phenothiazine derivative with benzoate-fluoroalkyl group on N and two phenyl groups]

-continued

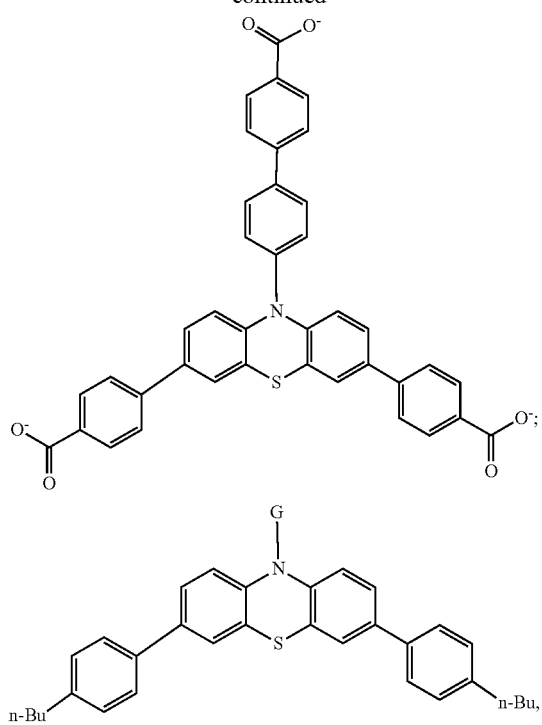

or salts thereof, wherein G is

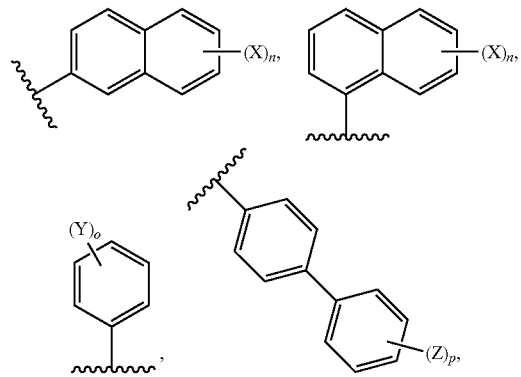

2. The compound of claim 1, wherein $A^1$, $A^2$ and $A^3$ are independently selected from the group consisting of:

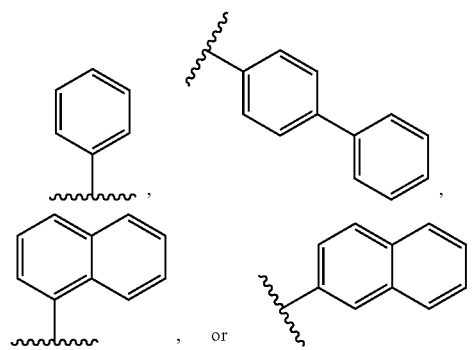

-continued

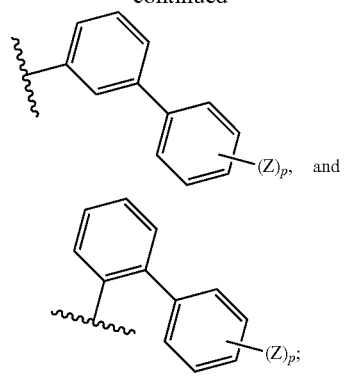

wherein each occurrence of X, Y, and Z is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)$_2$, OC(O)N(R)$_2$, and C(S)N(R)$_2$, n is an integer from 0 to 7;

o is an integer from 0 to 5; and p is an integer from 0 to 9.

3. The compound of claim 2, wherein $A^1$, $A^2$, and $A^3$ are independently selected from the group consisting of:

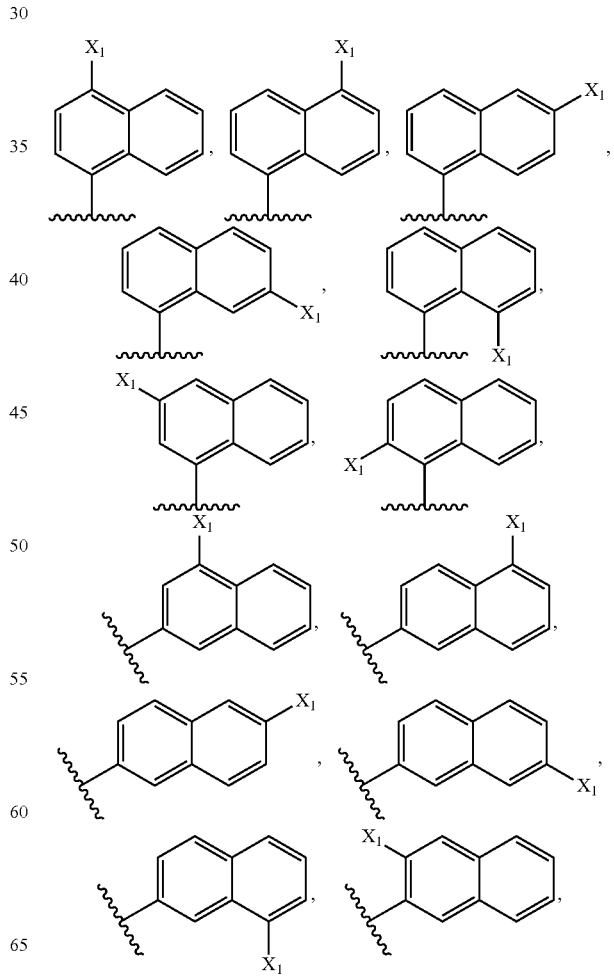

-continued

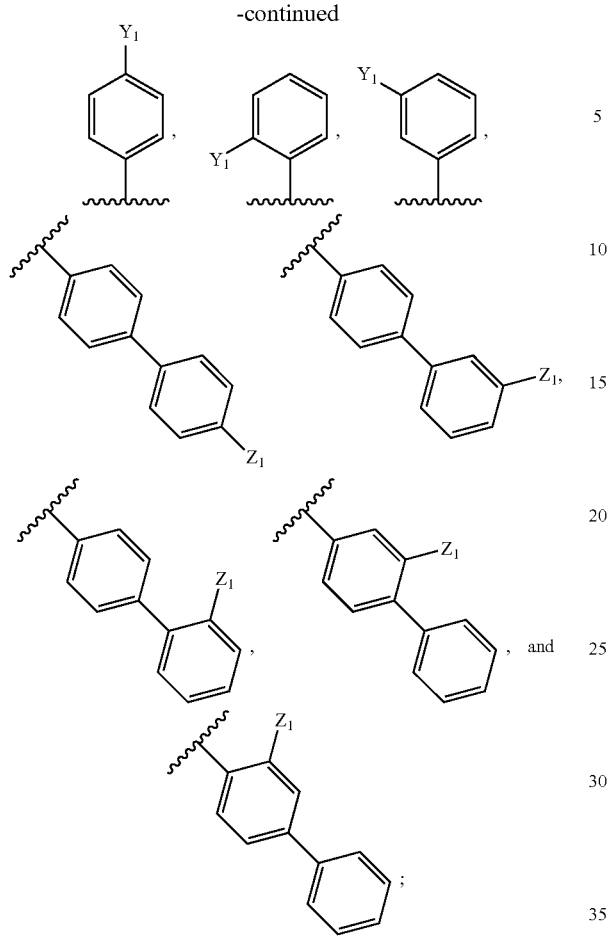

wherein each occurrence of $X_1$, $Y_1$, and $Z_1$ is independently selected from the group consisting of F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)$_2$, OC(O)N(R)$_2$, and C(S)N(R)$_2$.

4. The compound of claim 1, wherein $A^2$ and $A^3$ are $C_{6-12}$ aryl.

5. The compound of claim 4, wherein $A^2$ and $A^3$ are biaryl.

6. The compound of claim 5, wherein $A^2$ and $A^3$ are 4,4'-biphenyl.

7. The compound of claim 1, wherein $A^1$ is a $C_{10}$ aryl substituted by 1 to 7 groups selected from the group consisting of hydrogen, F, Cl, Br, I, OR, CN, NO, $NO_2$, $ONO_2$, $CF_3$, $OCF_3$, R, $N(R)_2$, SR, SOR, $SO_2R$, $SO_2N(R)_2$, $SO_3R$, C(O)R, C(S)R, C(O)OR, OC(O)R, C(O)N(R)$_2$, OC(O)N(R)$_2$, and C(S)N(R)$_2$.

8. The compound of claim 7, wherein $A^1$ is 1-naphthyl or 2-naphthyl.

9. The compound of claim 8, wherein $A^1$ is

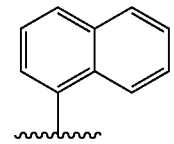

10. The compound of claim 7, wherein $A^1$ is 1-naphthyl or 2-naphthyl is mono-substituted by a group selected from the group consisting of F, Cl, Br, CN, and $NO_2$.

11. The compound of claim 10, wherein $A^1$ is substituted by F or CN.

12. The compound of claim 11, wherein $A^1$ is

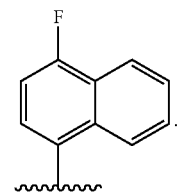 [SMILES: *c1ccc(F)c2ccccc12]

13. The compound of claim 11, wherein $A^1$ is

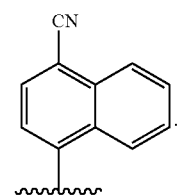

14. A photocatalyst comprising the compound of claim 1.

* * * * *

UNITED STATES PATENT AND TRADEMARK OFFICE
CERTIFICATE OF CORRECTION

PATENT NO.         : 11,905,267 B2
APPLICATION NO.    : 17/789874
DATED              : February 20, 2024
INVENTOR(S)        : Steven Sartor et al.

Page 1 of 1

It is certified that error appears in the above-identified patent and that said Letters Patent is hereby corrected as shown below:

On the Title Page

Item (72) The inventor's name should be spelled as follows:
Garret Miyake

Signed and Sealed this
Twenty-second Day of April, 2025

Coke Morgan Stewart
*Acting Director of the United States Patent and Trademark Office*